United States Patent
Ketner et al.

(10) Patent No.: US 8,372,836 B2
(45) Date of Patent: Feb. 12, 2013

(54) SPRAY DRIED FORMULATION

(75) Inventors: Rodney James Ketner, Bend, OR (US);
Douglas Alan Lorenz, Bend, OR (US);
David Keith Lyon, Bend, OR (US)

(73) Assignee: Bend Research, Inc., Bend, OR (US)

( * ) Notice: Subject to any disclaimer, the term of this patent is extended or adjusted under 35 U.S.C. 154(b) by 758 days.

(21) Appl. No.: 12/311,543

(22) PCT Filed: Oct. 8, 2007

(86) PCT No.: PCT/IB2007/003062
§ 371 (c)(1),
(2), (4) Date: Apr. 1, 2009

(87) PCT Pub. No.: WO2008/047201
PCT Pub. Date: Apr. 24, 2008

(65) Prior Publication Data
US 2010/0029667 A1    Feb. 4, 2010

Related U.S. Application Data

(60) Provisional application No. 60/829,720, filed on Oct. 17, 2006.

(51) Int. Cl.
*A61K 31/50* (2006.01)
*A61K 31/501* (2006.01)
*A61K 31/52* (2006.01)
*A01N 43/90* (2006.01)
*A01N 25/00* (2006.01)
*A01K 47/00* (2006.01)
*C07D 401/00* (2006.01)
*C07D 403/00* (2006.01)
*C07D 405/00* (2006.01)

(52) U.S. Cl. .............. 514/252.01; 514/263.37; 514/781; 544/238

(58) Field of Classification Search .................. None
See application file for complete search history.

(56) References Cited

U.S. PATENT DOCUMENTS 7,642,350 B2 * 1/2010 Pryde .............................. 544/61
2006/0216351 A1 * 9/2006 Friesen et al. ................. 424/484

* cited by examiner

*Primary Examiner* — Jeffrey S. Lundgren
*Assistant Examiner* — William Lee
(74) *Attorney, Agent, or Firm* — Chernoff Vilhauer McClung & Stenzel LLP

(57) ABSTRACT

Pharmaceutical compositions comprising a poorly water soluble ionizable drug, a cationic species and a dispersion polymer are disclosed, together with a process for forming the compositions. The neutral form of the drug has (i) a solubility of less than 1 mg/ml, in aqueous solution at a pH between 6 and 7, (ii) a solubility of less than 20 mg/mL in a volatile organic solvent, and (iii) an acidic pKa value of greater than 5. At least 90 wt % of the drug in the solid dispersion being in a non-crystalline form. The drug, the cationic species, and the dispersion polymer constitute at least 80 wt % of the solid dispersion.

7 Claims, 2 Drawing Sheets

SPRAY DRIED FORMULATION

This is a 371 of PCT/IB/2007/003062 filed 8 Oct. 2007, and claims priority of U.S. 60/829,720 filed 17 Oct. 2006.

FIELD OF THE INVENTION

This invention relates to pharmaceutical compositions comprising a solid dispersion of a poorly water soluble ionizable drug, a cationic species and a dispersion polymer, together with a process for forming the compositions. The neutral form of the drug has (i) a solubility of less than 1 mg/mL in aqueous solution at a pH between 6 and 7, (ii) a solubility of less than 20 mg/mL in a volatile organic solvent, and (iii) an acidic pKa value of greater than 5.

BACKGROUND OF THE INVENTION

It is well known that low solubility drugs may be formulated as a solid dispersion of a drug in a polymer to improve the bioavailability of poorly soluble drugs. Preferred solid dispersions are formed by spray drying, since this process results in dispersions in which the drug is typically present as non-crystalline drug dispersed homogeneously throughout the polymer. Such solid dispersions are also referred to as molecular dispersions or solid solutions. See, for example, J. Ford, "Current status of solid dispersions," *Pharm. Acta. Helv.* 61 (1986) 69-88.

Solvent processing is a preferred manufacturing technique for making solid dispersions. In this process, the drug and polymer are both dissolved in a common solvent. The solvent is then rapidly removed by atomizing the spray solution in the presence of a drying gas. The rapid removal of solvent results in a solid dispersion of the drug in a non-crystalline form (also referred to as amorphous) homogeneously dispersed through the polymer. Such solid dispersions provide high concentrations of dissolved drug in in vitro dissolution tests and good bioavailability.

However, there exists a class of compounds for which it is desired to form solid dispersions in order to improve bioavailability, but which are difficult to prepare as solid dispersions. Such compounds have very low aqueous solubility, as well as very poor solubility in the volatile solvents used to form the spray solution. As a result, such compounds may be impractical to prepare as solid dispersions using the spray drying technique.

Accordingly, it is desired to provide solid dispersions of drugs and polymers, the drug being both poorly aqueous soluble and poorly soluble in volatile organic solvents.

BRIEF SUMMARY OF THE INVENTION

In one aspect, a solid dispersion comprises (a) a poorly water soluble ionizable drug, the neutral form of the drug having (i) a solubility of less than 1 mg/mL in aqueous solution at a pH between 6 and 7, (ii) a solubility of less than 20 mg/mL in a volatile organic solvent, and (iii) an acidic pKa value of greater than 5; (b) a cationic species; (c) a dispersion polymer; (d) at least 90 wt % of the drug in the solid dispersion being in a non-crystalline form; and (e) the drug, the cationic species, and the dispersion polymer constitute at least 80 wt % of the solid dispersion.

In another aspect, the drug in its neutral form can exist in a keto/enol form.

In another aspect, the cationic species is selected from the group consisting of cations of potassium, sodium, calcium, magnesium, aluminum, ammonium, and mixtures thereof.

In another aspect, the dispersion polymer is selected from the group consisting of neutral polymers, neutralized polymers, and mixtures thereof.

In another aspect, the dispersion polymer is hydroxypropyl methylcellulose (HPMC).

In another aspect, a process for forming a solid dispersion comprises (a) forming a spray solution comprising a poorly water soluble ionizable drug, a dispersion polymer, a base, and a solvent; (b) the neutral form of the drug having (i) a solubility of less than 1 mg/mL in aqueous solution at a pH between 6 and 7, (ii) a solubility of less than 20 mg/mL in a volatile organic solvent, and (iii) an acidic pKa value of greater than 5; (b) evaporating the solvent to form the solid dispersion, the solid dispersion comprising the drug, a cationic species, and the dispersion polymer; (d) at least 90 wt % of the drug in the solid dispersion being in a non-crystalline form; and (e) the drug, the cationic species, and the dispersion polymer constitute at least 80 wt % of the solid dispersion.

In another aspect, the drug is 6-amino-9-benzyl-8-oxo-8,9-dihydro-7H-purine-2-carboxylic acid cyclopropylmethylamide.

In another aspect, the drug is 4-amino-1-benzyl-6-trifluoromethyl-1,3-dihydro-imidazo[4,5-c]pyridine-2-one.

In still another aspect, the drug is 6-(5-chloro-3-methyl-benzofuran-2-sulfonyl)-2H-pyridazin-3-one.

The inventors have solved the problem of forming dispersions of drugs that are weakly acidic and poorly soluble in volatile organic solvents by codissolving the drug and a base in a volatile organic solvent, thereby effectively forming the ionized form of the drug in the organic solvent. The higher solubility of the drug in the ionized form in the volatile solvent results in significantly improved manufacturing of the solid dispersion.

The inventors have further identified that the physical stability of the compositions of the present invention can be significantly improved by storing the compositions under relatively dry conditions.

The foregoing and other objectives, features, and advantages of the invention will be more readily understood upon consideration of the following detailed description of the invention.

DETAILED DESCRIPTION OF THE INVENTION

Figure 1:
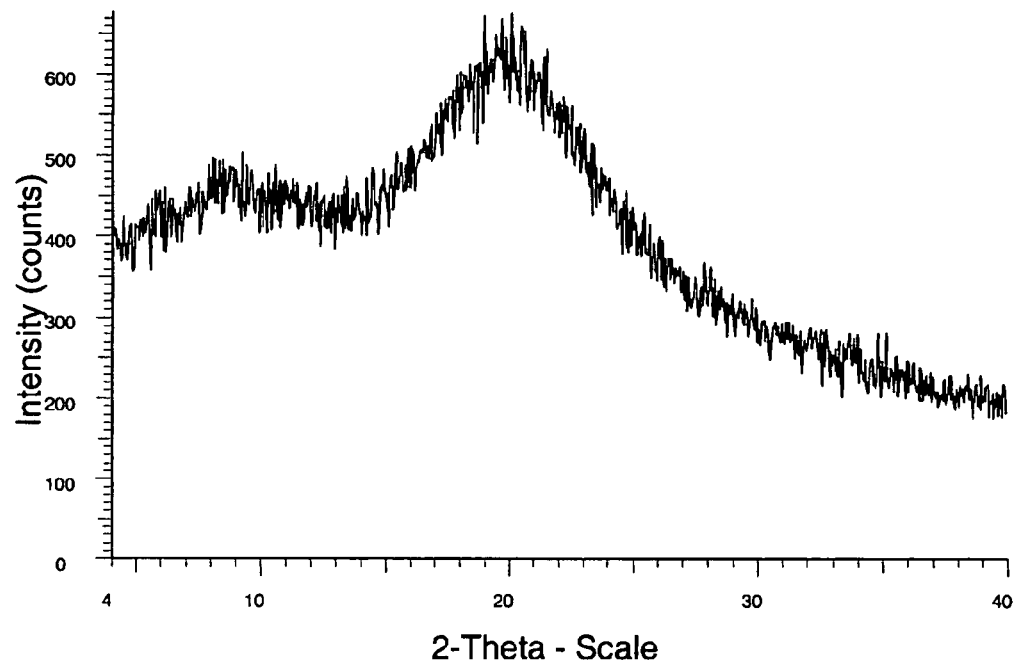
FIG. 1 shows a Powder X-Ray Diffraction (PXRD) diffractogram of the solid dispersion of Example 3.

The compositions of the present invention comprise a solid dispersion of a drug, a dispersion polymer and a cationic species. The drug, solid dispersions, dispersion polymers, methods for forming the dispersions, and dosage forms containing the compositions of the present invention, are described in more detail below.

The Drug

The present invention is suitable for use with any drug that is poorly aqueous soluble, poorly soluble in volatile organic solvents, and that is weakly acidic.

By "poorly aqueous soluble" is meant that the drug has a solubility of less than 1 mg/ml in aqueous solution at a pH of between 6 and 7. The invention has increasing utility as the aqueous solubility decreases. The drug may have an aqueous solubility of less than 0.5 mg/ml, less than 0.1 mg/ml, less than 0.05 mg/ml, or even less than 0.01 mg/ml. Solubility may be measured at 25° C. in water or a phosphate buffered saline (PBS) solution adjusted to a pH between 6 and 7.

The drug is poorly soluble in volatile organic solvents. By "volatile organic solvent" is meant a solvent selected from the group consisting of acetone, methanol, tetrahydrofuran, ethyl acetate, mixtures of any one of these with water, and mixtures of these with each other. By "poorly soluble" is meant that the drug has a solubility of less than 20 mg/mL in each of the following: acetone, methanol, tetrahydrofuran, ethyl acetate, mixtures of any one of these with water, and mixtures of these with each other. As used herein, the solubility is assumed to be measured at ambient temperature and pressure. The invention finds increasing utility as the solubility of the drug in the volatile organic solvent decreases. Thus, the drug may have a solubility in the volatile organic solvent of less than 15 mg/mL, or less than 10 mg/mL, or even less than 5 mg/mL at ambient temperature and pressure.

Drugs that are both poorly aqueous soluble and poorly soluble in volatile organic solvents often have a relatively melting point temperature ($T_m$). In one embodiment, the drug has a $T_m$ of greater than 200° C. The $T_m$ may be greater than 250° C., or even greater than 300° C.

Such drugs often have a relatively high ratio of $T_m$ to glass transition temperature ($T_g$). In one embodiment, the drug has a $T_m/T_g$ ratio (in K/K) of greater than 1.4. The $T_m/T_g$ ratio (in K/K) may be greater than 1.45, or even greater than 1.5.

Such drugs also tend to have a moderate to low hydrophobicity. Log P, defined as the base 10 logarithm of the ratio of (1) the drug concentration in an octanol phase to (2) the drug concentration in a water phase when the two phases are in equilibrium with each other, is a widely accepted measure of hydrophobicity. By "moderate to low hydrophobicity" is meant that the drug has a Log P value of less than 4.5. The invention finds greater utility for drugs with even lower Log P values. Thus, the Log P value may be less than 4.0, less than 3.5, and even less than 3.0.

Log P may be measured experimentally or calculated using methods known in the art. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (27 *J. Chem. Inf. Comput. Sci.* 21 (1987)); Viswanadhan's fragmentation method (29 *J. Chem. Inf. Comput. Sci.* 163 (1989)); or Broto's fragmentation method (19 *Eur. J. Med. Chem.-Chim. Theor.* 71 (1984)).

By "weakly acidic" is meant that the drug has an acidic pKa of greater than 5. Here, the term $pK_a$ is used in its traditional form, the $pK_a$ being the negative logarithm of the acid ionization constant. Unless otherwise noted, the $pK_a$ is assumed to be measured in distilled water at 25° C. The drug may have an acidic pKa that is greater than 6, greater than 6.5, or may even have an acidic pKa of greater than 7.

Such drugs typically have a structural feature in which an oxy anion can be delocalized through a conjugated system. One exemplary class of structural features is compounds that can exist in keto/enol forms. The keto and enol forms of such compounds are commonly referred to as tautomers; the only difference in the structures being the placement of a proton. At equilibrium, most molecules exist in both keto and enol forms, the ratio of keto to enol forms being dependent on the other structural features of the molecule and the immediate environment of the molecule. When a molecule that can exist in a keto/enol form is placed in an environment where the pH is greater than the pKa of the molecule, the keto or enol group will exchange a proton with the base, resulting in the formation of an enolate anion, as represented by the following scheme:

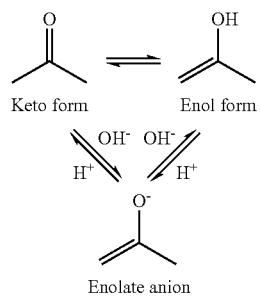

See J. R. Keeffe, in *The Chemistry of Enols,* 1990 for details regarding keto/enol compounds.

Several common structural features can form an oxy anion that is delocalized through a conjugated system. In the following, the "R" substituent can represent a hydrogen atom, a carbon atom, an oxygen atom, a nitrogen atom, a sulfur atom, or an aromatic or aliphatic structure. For structures with more than one R group, the R groups can be the same or different. Specific examples of structural features in which the oxy anion is delocalized through a conjugated system include:

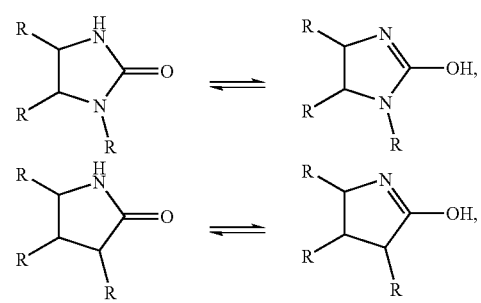

-continued
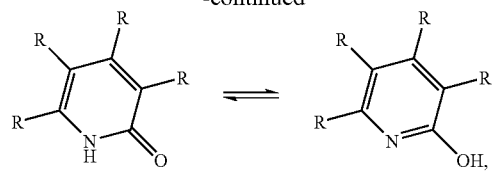
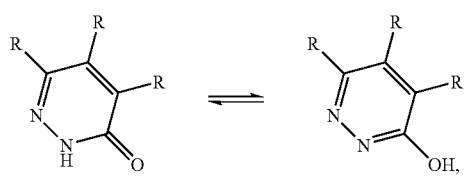
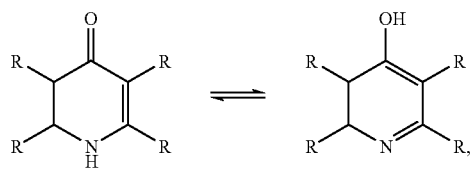
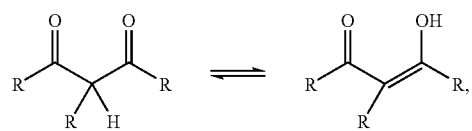
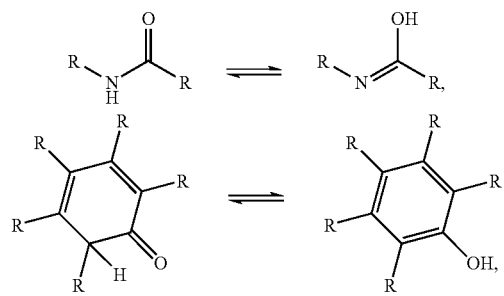
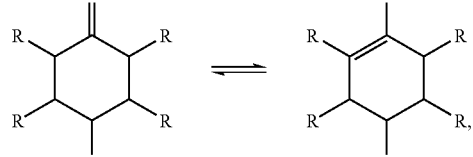
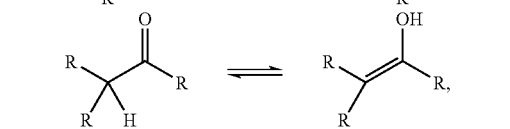
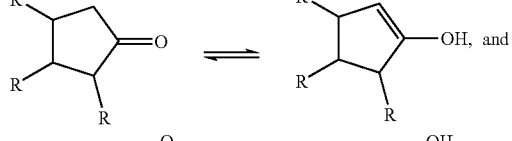
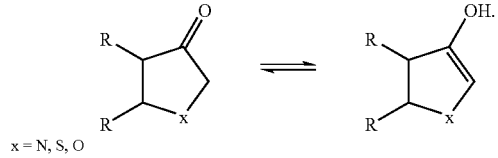
x = N, S, O
In one embodiment, the drug contains the structural feature
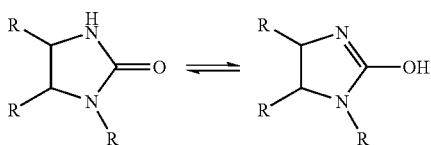
In another embodiment, the drug contains the structural feature
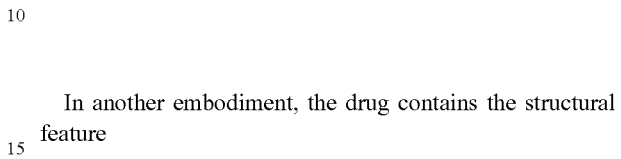
In another embodiment, the drug contains the structural feature
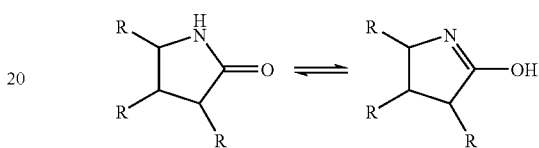
In another embodiment, the drug contains the structural feature
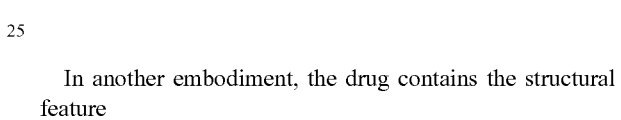
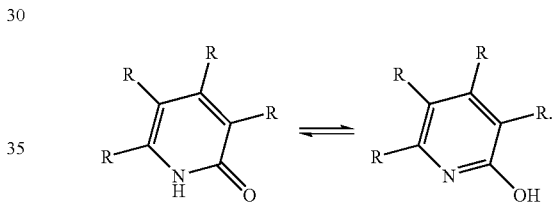
In another embodiment, the drug contains the structural feature
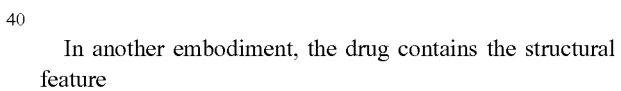
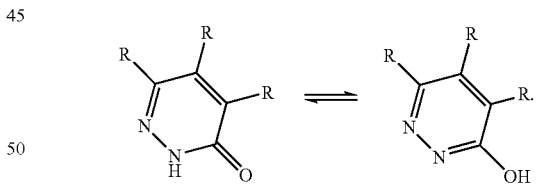
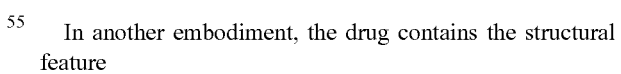
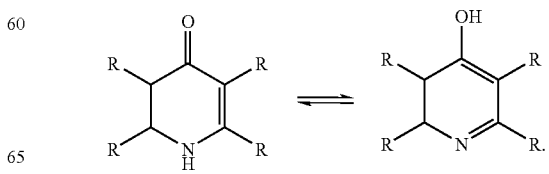

In another embodiment, the drug contains the structural feature

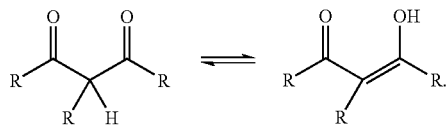

In another embodiment, the drug contains the structural feature

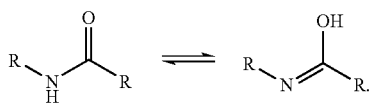

In another embodiment, the drug contains the structural feature

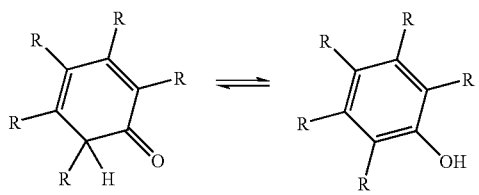

In another embodiment, the drug contains the structural feature

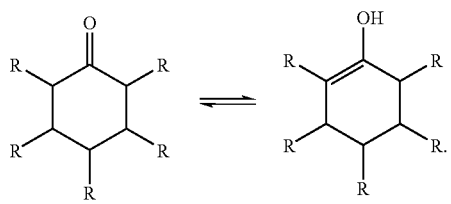

In another embodiment, the drug contains the structural feature

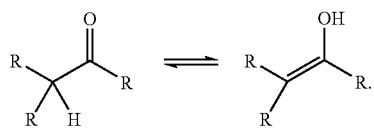

In another embodiment, the drug contains the structural feature

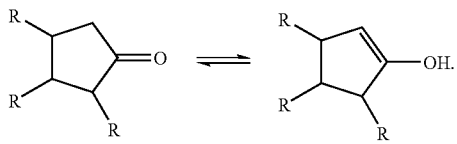

In another embodiment, the drug contains the structural feature

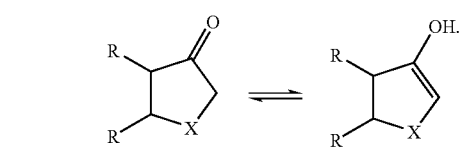

x = N, S, O

Each named drug should be understood to include any pharmaceutically acceptable forms of the drug. By "pharmaceutically acceptable forms" is meant any pharmaceutically acceptable derivative or variation, including tautomers, stereoisomers, stereoisomer mixtures, enantiomers, solvates, hydrates, isomorphs, polymorphs, pseudomorphs, neutral forms, salt forms and prodrugs.

In one embodiment, the drug is 6-amino-9-benzyl-8-oxo-8,9-dihydro-7H-purine-2-carboxylic acid cyclopropylmethyl-amide ("Drug 1"), or pharmaceutically acceptable forms thereof, having the following structure in its neutral form:

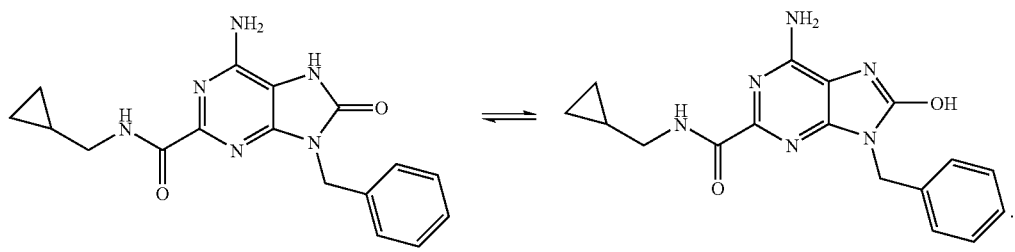 [SMILES: Nc1nc(C(=O)NCC2CC2)nc2c1[nH]c(=O)n2Cc1ccccc1 ; Nc1nc(C(=O)NCC2CC2)nc2c1nc(O)n2Cc1ccccc1]

In another embodiment, the drug is 4-amino-1-benzyl-6-trifluoromethyl-1,3-dihydro-imidazo[4,5-c]pyridin-2-one ("Drug 2"), or pharmaceutically acceptable forms thereof, having the following structure in its neutral form:

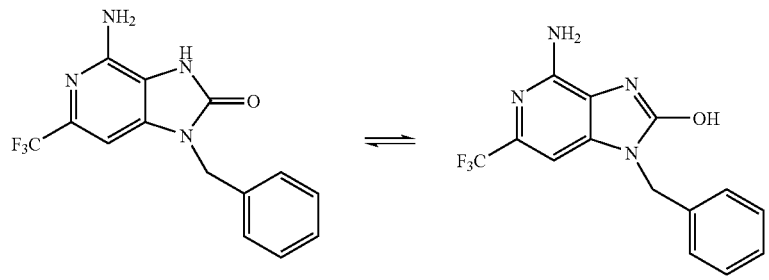 [SMILES: Nc1nc(C(F)(F)F)cc2c1[nH]c(=O)n2Cc1ccccc1 ; Nc1nc(C(F)(F)F)cc2c1nc(O)n2Cc1ccccc1]

In another embodiment the drug is 6-(5-chloro-3-methyl-benzofuran-2-sulfonyl)-2H-pyridazin-3-one ("Drug 3"), or pharmaceutically acceptable forms thereof, having the following structure in its neutral form:

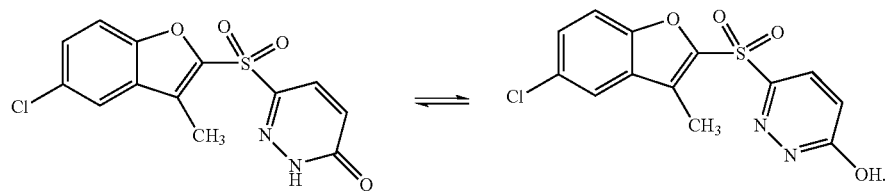 [SMILES: Cc1c(S(=O)(=O)c2ccc(=O)[nH]n2)oc2ccc(Cl)cc12 ; Cc1c(S(=O)(=O)c2ccc(O)nn2)oc2ccc(Cl)cc12]

Cationic Species

As described above, drugs suitable for use in this invention are poorly water soluble. Because of this, it is desirable to formulate the drugs into solid dispersions to improve solubility and bioavailability. However, because the drugs are poorly soluble in volatile organic solvents, processing the drugs into a solid dispersion by solvent processing can be impractical.

The inventors have found that when a drug of the present invention is present in a pharmaceutically acceptable ionized form, its solubility in volatile organic solvents is significantly increased relative to the neutral form of the drug. This higher solubility leads to improved manufacturability and processing of the compound into an efficacious formulation.

Because the drugs are weakly acidic they will form ionized forms in the presence of a base, the base providing the cationic counterion for the anionic drug form. The ionized form of the drug has a significantly higher solubility in volatile organic solvents than the neutral form of the drug. For example, the solubility of the crystalline potassium salt form of the Drug 1 in a 90/10 (w/w) methanol/water mixture is greater than 5 mgA/mL, while the solubility of the crystalline neutral form of Drug 1 in methanol is about 0.059 mgA/mL (as used herein, "mgA" means milligrams of active drug as present as the neutral form). This 85-fold higher solubility results in improved manufacturability and processing as discussed herein below.

A wide range of bases may be used to form the ionized form of the drug in a volatile organic solvent. The term "base" is used broadly to include not only strong bases such as sodium hydroxide, but also weak bases and buffers that are capable of achieving the desired degree of ionization. Generally, the base should have a pKa value that is greater than the pKa value of the drug. Thus, the base should have a pKa value greater than about 6, more preferably greater than about 7, and most preferably greater than about 8.

Examples of bases include hydroxides, such as sodium hydroxide, calcium hydroxide, potassium hydroxide, magnesium hydroxide, ammonium hydroxide, and choline hydroxide; bicarbonates, such as sodium bicarbonate, potassium bicarbonate, and ammonium bicarbonate; carbonates, such as ammonium carbonate, calcium carbonate, and sodium carbonate; oxides, such as magnesium oxide and calcium oxide; amines, such as tris(hydroxymethyl)amino methane, ethanolamine, diethanolamine, N-methyl glucamine, glucosamine, ethylenediamine, N,N'-dibenzylethylenediamine, N-benzyl-2-phenethylamine, cyclohexylamine, cyclopentylamine, diethylamine, isopropylamine, diisopropylamine, dodecylamine, and triethylamine; proteins, such as gelatin; amino acids such as lysine, arginine, guanine, glycine, and adenine; polymeric amines, such as polyamino methacrylates, such as Eudragit E; conjugate bases of various acids, such as sodium acetate, potassium acetate, sodium benzoate, ammonium acetate, disodium phosphate, trisodium phosphate, dipotassium phosphate (potassium phosphate dibasic), tripotassium phosphate (potassium phosphate tribasic), calcium hydrogen phosphate, sodium phenolate, sodium sulfate, ammonium chloride, ammonium sulfate; salts of tetra sodium ethylenediamine tetraacetic acid (EDTA), such as tetra sodium EDTA; and salts of various acidic polymers such as sodium starch glycolate, sodium carboxymethyl cellulose and sodium polyacrylic acid.

When the base is codissolved with the drug in a volatile organic solvent, the ionized form of the drug forms; the counterion to the ionized form of the drug being the cationic species supplied by the base that is codissolved with the drug. Preferably, the cationic species is selected from the group consisting of cations of the following: potassium, sodium, calcium, magnesium, aluminum, ammonium, benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, and mixtures thereof. More preferably, the cationic species is selected from the group consisting of cations of potassium, sodium, calcium, magnesium, aluminum, ammonium, and mixtures thereof.

In one embodiment, the cationic species is selected from cations of potassium, sodium, and mixtures thereof.

Dispersion Polymers

Dispersion polymers suitable for use in the compositions of the present invention should be pharmaceutically acceptable, and should have at least some solubility in aqueous solution at physiologically relevant pHs (e.g. 1 to 8). Almost any polymer that has an aqueous-solubility of at least about 0.1 mg/mL over at least a portion of the pH range of 1 to 8 may be suitable.

In one embodiment, the polymer is a neutral or non-ionizable polymer, meaning that the polymer possesses substantially no ionizable functional groups. By "substantially no ionizable functional groups" is meant that the number of ionizable groups covalently attached to the polymer is less than about 0.05 milliequivalents per gram of polymer. Preferably, the number is less than about 0.02 milliequivalents per gram of neutral polymer. By "ionizable groups" is meant functional groups that are at least about 10% ionized over at least a portion of the physiologically relevant pH range of 1 to 8. Such groups have pKa values of about 0 to 9.

One class of neutral polymers suitable for use with the present invention comprises neutral non-cellulosic polymers. Exemplary polymers include: vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; acrylate and methacrylate copolymers; polyethylene polyvinyl alcohol copolymers; and polyoxyethylene-polyoxypropylene block copolymers (also referred to as poloxamers).

Another class of neutral polymers suitable for use with the present invention comprises neutral cellulosic polymers. By "cellulosic" is meant a cellulose polymer that has been modified by reaction of at least a portion of the hydroxyl groups on the saccharide repeat units with a compound to form an ester or an ether substituent. Exemplary neutral cellulosic polymers that may be used as the polymer include: hydroxypropyl methyl cellulose acetate (HPMCA), hydroxypropyl methyl cellulose (HPMC), hydroxypropyl cellulose (HPC), methyl cellulose, hydroxyethyl methyl cellulose, hydroxyethyl cellulose, hydroxyethyl cellulose acetate, and hydroxyethyl ethyl cellulose.

In another embodiment, the polymer is a neutralized acidic polymer. Neutralized acidic polymers are described in more detail in the U.S. Published Patent Application US 2003-0054038, entitled "Pharmaceutical Compositions of Drugs and Neutralized Acidic Polymers" filed Jun. 17, 2002, the relevant disclosure of which is incorporated by reference. By "acidic polymer" is meant any polymer that possesses a significant number of acidic moieties. In general, a significant number of acidic moieties would be greater than or equal to about 0.05 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer that has a pKa of less than about 10.

By "neutralized acidic polymer" is meant any acidic polymer for which a significant fraction of the "acidic moieties" or "acidic substituents" have been "neutralized"; that is, exist in their deprotonated form. The "degree of neutralization," $\alpha$, of a polymer substituted with monoprotic acids (such as carboxylic acids) is defined as the fraction of the acidic moieties on the polymer that have been neutralized; that is, deprotonated by a base.

Typically, for an acidic polymer to be considered a "neutralized acidic polymer," α must be at least about 0.01 (or 1%), more preferably at least about 0.1 (10%), even more preferably at least about 0.5 (50%), and most preferably at least 0.9 (meaning that at least 90% of the acidic moieties have been neutralized).

Exemplary acidic polymers that may be used in the present invention in a neutralized form include: hydroxypropyl methyl cellulose acetate succinate (HPMCAS), hydroxypropyl methyl cellulose phthalate (HPMCP), carboxymethylethyl cellulose (CMEC), cellulose acetate phthalate (CAP), cellulose acetate succinate (CAS), hydroxypropyl methyl cellulose acetate phthalate (HPMCAP), cellulose acetate trimellitate (CAT), hydroxypropyl methyl cellulose acetate trimellitate (HPMCAT), and carboxymethylcellulose acetate butyrate (CMCAB).

Neutralized acidic polymers may be formed by any conventional method known in the art that results in the desired degree of neutralization. In general, the acidic polymer is neutralized through the addition of a sufficient amount of base to a solution or composition containing the acidic polymer. For example, a base may be added to a solution of the acidic polymer resulting in neutralization of the polymer's acidic functional groups. Suitable bases that may be used to neutralize an acidic polymer include those listed above for the cationic species present in the solid dispersions of the invention.

In one embodiment, the base utilized to neutralize the polymer is the same base used to provide the cationic species present in the solid dispersions of the invention.

In one embodiment, the acidic polymer is neutralized prior to formation of the solid dispersion. In another embodiment, the acidic polymer is neutralized in the solvent solution used to form the solid dispersion, as discussed herein below.

While specific polymers have been discussed as being suitable for use in the compositions of the present invention, blends of such polymers may also be suitable. Thus the term "polymer" is intended to include blends of polymers in addition to a single species of polymer.

In one embodiment, the dispersion polymer is selected from the group consisting of a neutral polymer, a neutralized acidic polymer, or mixtures thereof.

In another embodiment, the dispersion polymer is selected from the group consisting of vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; acrylate and methacrylate copolymers; polyethylene polyvinyl alcohol copolymers; polyoxyethylene-polyoxypropylene block copolymers (also referred to as poloxamers); hydroxypropyl methyl cellulose acetate (HPMCA); hydroxypropyl methyl cellulose (HPMC); hydroxypropyl cellulose (HPC); methyl cellulose; hydroxyethyl methyl cellulose; hydroxyethyl cellulose; hydroxyethyl cellulose acetate; hydroxyethyl ethyl cellulose; neutralized forms of hydroxypropyl methyl cellulose acetate succinate (HPMCAS), neutralized forms of hydroxypropyl methyl cellulose phthalate (HPMCP), neutralized forms of carboxymethyl ethylcellulose (CMEC), neutralized forms of cellulose acetate phthalate (CAP), neutralized forms of cellulose acetate succinate (CAS), neutralized forms of hydroxypropyl methyl cellulose acetate phthalate (HPMCAP), neutralized forms of cellulose acetate trimellitate (CAT), neutralized forms of hydroxypropyl methyl cellulose acetate trimellitate (HPMCAT), neutralized forms of carboxymethylcellulose acetate butyrate (CMCAB), and mixtures thereof.

In yet another embodiment, the dispersion polymer is selected from the group consisting of hydroxypropyl methylcellulose (HPMC), hydroxypropyl methylcellulose acetate (HPMCA), hydroxypropyl cellulose (HPC), poloxamers, neutralized forms of hydroxypropyl methylcellulose acetate succinate (HPMCAS), neutralized forms of hydroxypropyl methylcellulose phthalate (HPMCP), neutralized forms of cellulose acetate phthalate (CAP), neutralized forms of cellulose acetate trimellitate (CAT), neutralized forms of carboxymethyl ethyl cellulose (CMEC), and mixtures thereof.

In yet another embodiment, the dispersion polymer is selected from the group consisting of HPMC, HPMCA, HPC, poloxamers, and mixtures thereof.

In still another embodiment, the dispersion polymer is selected from the group consisting of neutralized forms of the acidic polymers HPMCAS, HPMCP, CAP, CAT, CMEC, and mixtures thereof.

In still another embodiment, the dispersion polymer is HPMC.

In still another embodiment, the dispersion polymer is a neutralized form of HPMCAS.

In yet another embodiment, the dispersion polymer is HPMC and the cationic species is selected from the group consisting of cations of potassium, sodium, calcium, magnesium, aluminum, ammonium, and mixtures thereof.

In another embodiment, the dispersion polymer is HPMC and the cationic species is potassium.

In another embodiment, the dispersion polymer is HPMC and the cationic species is sodium.

In another embodiment, the dispersion polymer is HPMC and the cationic species is calcium.

In another embodiment, the dispersion polymer is HPMC and the cationic species is magnesium.

In another embodiment, the dispersion polymer is HPMC and the cationic species is aluminum.

In another embodiment, the dispersion polymer is HPMC and the cationic species is ammonium.

In yet another embodiment, the dispersion polymer is neutralized HPMCAS and the cationic species is selected from the group consisting of cations of potassium, sodium, calcium, magnesium, aluminum, ammonium, and mixtures thereof.

In another embodiment, the dispersion polymer is neutralized HPMCAS and the cationic species is potassium.

In another embodiment, the dispersion polymer is neutralized HPMCAS and the cationic species is sodium.

In another embodiment, the dispersion polymer is neutralized HPMCAS and the cationic species is calcium.

In another embodiment, the dispersion polymer is neutralized HPMCAS and the cationic species is magnesium.

In another embodiment, the dispersion polymer is neutralized HPMCAS and the cationic species is aluminum.

In another embodiment, the dispersion polymer is neutralized HPMCAS and the cationic species is ammonium.

Solid Dispersions

The pharmaceutical compositions described herein comprise a solid dispersion of the drug, a dispersion polymer, and a cationic species. By "solid dispersion" is meant that at least a portion of the drug is dispersed in the polymer. Such solid dispersions are often referred to in the art as "molecular dispersions" or "solid solutions" of drug in the polymer.

While the drug in its pure form may be either crystalline or non-crystalline, at least 90 wt % of the drug in the solid dispersion is non-crystalline. The term "crystalline," as used herein, means a particular solid form of a compound that exhibits long-range order in three dimensions. "Non-crystalline" refers to material that does not have long-range three-dimensional order, and is intended to include not only material which has essentially no order, but also material which may have some small degree of order, but the order is in less than three dimensions and/or is only over short distances. Another term for a non-crystalline form of a material is the "amorphous" form of the material. Preferably at least about 95 wt % of the drug in the solid dispersion is non-crystalline; in other words, the amount of drug in crystalline form does not exceed about 5 wt %. Amounts of crystalline and non-crystalline drug may be characterized by techniques known in the art such as Powder X-Ray Diffraction (PXRD) crystallography, Scanning Electron Microscope (SEM) analysis, solid state NMR, or thermal techniques such as differential scanning calorimetry (DSC), or any other standard quantitative measurement.

The non-crystalline drug in the solid dispersion can exist as a pure phase, as a solid solution of drug homogeneously distributed throughout the dispersion polymer, or any combination of these states or those states that lie between them. Preferably, at least a portion of the drug and the dispersion polymer is present in the nanoparticle in the form of a solid solution. The solid solution may be thermodynamically stable, in which the drug is present at less than the solubility limit of the drug in the dispersion polymer, or may be a supersaturated solid solution in which the drug exceeds its solubility limit in the dispersion polymer. Preferably essentially all of the drug and the dispersion polymer is present as a solid solution.

When the non-crystalline drug and the dispersion polymer have glass transition temperatures that differ by more than about 20° C., the fraction of drug present in relatively pure non-crystalline domains or regions within the solid dispersion can be determined by measuring the glass transition temperature ($T_g$) of the dispersion. $T_g$ as used herein is the characteristic temperature at which a glassy material, upon gradual heating, undergoes a relatively rapid (i.e., in 10 to 100 seconds) physical change from a glassy state to a rubbery state. The $T_g$ of a non-crystalline material such as a polymer or dispersion can be measured by several techniques, including by a dynamic mechanical analyzer (DMA), a dilatometer, a dielectric analyzer, and by DSC. The exact values measured by each technique can vary somewhat, but usually fall within 10° to 30° C. of each other. When the solid dispersion exhibits a single $T_g$, the amount of drug in pure non-crystalline domains or regions in the dispersion is generally less than about 10 wt %, confirming that the dispersion is substantially homogeneous. This is in contrast to a simple physical mixture of particles of pure non-crystalline drug and pure dispersion polymer particles, which generally display two distinct $T_g$s, one being that of the drug and the other that of the polymer. For a solid dispersion that exhibits two distinct $T_g$s, it may be concluded that at least a portion of the drug is present in relatively pure non-crystalline domains. With DSC, the amount of drug present in relatively pure non-crystalline domains or regions may be determined by first measuring the $T_g$ of a substantially homogeneous dispersion with a known amount of drug to be used as a calibration standard. From the $T_g$ of a homogeneous dispersion, the $T_g$ of pure polymer, and the $T_g$ of the polymer-rich phase of a dispersion exhibiting two $T_g$s, the fraction of drug in relatively pure non-crystalline domains or regions can be estimated. Alternatively, the amount of drug present in relatively pure non-crystalline domains or regions may be determined by comparing the magnitude of the heat capacity (1) that correlates to the $T_g$ of the drug with (2) that which correlates to the $T_g$ of a physical mixture of non-crystalline drug and the polymer.

Preferably, the solid dispersion exhibits at least one $T_g$ that is different from the $T_g$ of pure drug and the $T_g$ of pure dispersion polymer, indicating that at least a portion of the drug and polymer are present as a solid solution.

The amount of dispersion polymer relative to the amount of drug present in the dispersion of the present invention depends on the characteristics of the polymer and may vary widely from a drug-to-polymer weight ratio of from 0.01 (1 part drug to 100 parts polymer) to about 3 (i.e., from 1 wt % drug to 75 wt % drug). Preferably, the drug-to-polymer weight ratio ranges from 0.01 to 2 (from 1 wt % drug to 66 wt % drug), and more preferably from 0.05 to 1 (from 5 wt % drug to 50 wt % drug).

In one embodiment, the solid dispersion comprises at least about 1 wt % drug, or a pharmaceutically acceptable form thereof. In another aspect, the solid dispersion comprises at least about 5 wt %, at least about 10 wt %, at least about 15 wt %, at least about 20 wt %, at least about 25 wt %, at least about 30 wt %, at least about 35 wt %, at least about 40 wt %, or at least about 45 wt % drug, or a pharmaceutically acceptable form thereof.

In another embodiment, the drug, the cationic species, and the dispersion polymer constitute at least 80 wt % of the total mass of the solid dispersion. Preferably the drug, the cationic species, and the dispersion polymer constitute at least 85 wt %, more preferably at least 90 wt %, and even more preferably at least 95 wt % of the total mass of the solid dispersion. In another embodiment the solid dispersion consists essentially of the drug, the cationic species, and the dispersion polymer.

In yet another embodiment, the solid dispersion consists of a plurality of particles, each of said particles comprising the drug, the cationic species, and the dispersion polymer. This is in contrast to a simple physical mixture of drug and a polymer, in which the drug is mixed, blended, or dispersed with a polymer to form a composition consisting of a mixture of particles of drug and particles of the polymer. In a preferred embodiment, the solid dispersion consists of a plurality of particles, each of the particles comprising the drug, the cationic species, and the dispersion polymer, and in which the drug, the cationic species, and the dispersion polymer are in the form of a solid solution.

Solid dispersions of the present invention provide good physical stability. As used herein, "physically stable" or "physical stability" means the tendency of non-crystalline drug present in the solid dispersion to crystallize at ambient storage conditions of 25° C. and less than about 60% RH. Thus, a solid composition that is more physically stable than another will have a slower rate of crystallization of the drug in the solid composition. Specifically, compositions of this invention have sufficient stability that less than about 10 wt % of the drug crystallizes during storage for 3 weeks at 25° C. and 60% RH. Preferably, less than about 5 wt % of the drug crystallizes during storage for 3 weeks at 25° C. and 60% RH, and more preferably, after storage for 3 months at 25° C. and 60% RH.

The inventors have found that the physical stability of solid dispersions of drugs and a dispersion polymer of the present invention is generally improved when the composition is stored under dry conditions. By "dry conditions" is meant that the solid dispersion is stored in an environment wherein the temperature is about 50° C. or less, and the relative humidity is about 50% or less, preferably about 30% or less, more preferably about 20% or less, and most preferably about 10% or less.

Preparation of Compositions

Solid dispersions comprising a drug, a cationic species, and a dispersion polymer may be made according to any conventional process that results in at least a portion of the drug being in the non-crystalline state. Such processes include solvent processes such as non-solvent precipitation, spray-coating and spray-drying.

Solvent processes generally consists of dissolution of at least a portion of the drug and at least a portion of the one or more dispersion polymer components in a common solvent. The term "solvent" is used broadly and includes mixtures of solvents. "Common" here means that the solvent, which can be a mixture of compounds, will dissolve at least a portion of the drug and the dispersion polymer(s). Preferably, the solvent dissolves essentially all of the drug and essentially all of the dispersion polymer. As discussed above, a base is generally co-dissolved with the drug in the solvent to increase the solubility of the drug in the solvent.

Solvents suitable for solvent processing can be any compound in which the ionized form of the drug and the dispersion polymer are mutually soluble. Preferably, the solvent is also volatile with a boiling point of 150° C. or less. In addition, the solvent should have relatively low toxicity and be removed from the solid dispersion to a level that is acceptable according to The International Committee on Harmonization (ICH) guidelines. Removal of solvent to this level may require a subsequent processing step such as tray-drying. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, 1,1,1-trichloroethane, and tetrahydrofuran. Lower volatility solvents such as dimethyl acetamide or dimethylsulfoxide can also be used in small amounts in mixtures with a volatile solvent. Mixtures of solvents, such as 50% methanol and 50% acetone, can also be used, as can mixtures with water, so long as the polymer and the drug are sufficiently soluble to make the spray-drying process practicable. Preferred solvents are methanol, acetone, tetrahydrofuran, ethyl acetate, mixtures of these with water, and mixtures thereof.

In a preferred embodiment, the ionized form of the drug is formed in situ in the solvent, as described herein. In this process the neutral form of the drug and a base are co-dissolved or suspended in a solvent. Because the ionized form of the drug has a higher solubility in the solvent, this process allows for a higher concentration of the drug to be dissolved in the solvent, increasing throughput during the solvent process.

Preferably a sufficient amount of base is co-dissolved with the drug in the solvent such that a major portion of the drug is present in the final solution as the ionized form, meaning that at least about 60 wt % of the drug in the final solution is present as the ionized form. Preferably a sufficient amount of base is co-dissolved such that at least about 70 wt % of the drug in the final solution is present as the ionized form, more preferably at least about 80 wt %, even more preferably at least about 90 wt %, and most preferably at least about 95 wt % of the drug is present as the ionized form. In one embodiment, essentially all of the drug in the final solution is present as the ionized form.

The amount of base required to be co-dissolved with the drug in the solvent to convert the drug to the ionized form will depend on the properties of the base selected, and in particular with the $pK_a$ of the base. Generally, for a strong base (with a pKa of about 9 or greater), one mole of base will convert one mole of the drug to the ionized form. For example, to form a solution in which essentially all of the drug was in the ionized form, equal moles of the drug and a strong base would be co-dissolved in the solvent. In one embodiment, an excess of base is added to the solvent to ensure essentially all of the drug is in the ionized form.

When a neutralized dispersion polymer is formed in situ along with the ionized form of the drug, a sufficient amount of base is added to provide the desired amount of the ionized form of the drug and the desired amount of neutralized dispersion polymer.

After at least a portion of each of the drug and dispersion polymer have been dissolved, the solvent is removed by evaporation or by mixing with a non-solvent. Exemplary processes are spray-drying, spray-coating (pan-coating, fluidized bed coating, etc.), and precipitation by rapid mixing of the drug and dispersion polymer solution with $CO_2$, hexane, heptane, water of appropriate pH, or some other non-solvent. Preferably, removal of the solvent results in a solid dispersion that is substantially homogeneous. To achieve this end, it is generally desirable to rapidly remove the solvent from the solution such as in a process where the solution is atomized and the drug and the dispersion polymer rapidly solidify.

The solvent may be removed by spray-drying. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's *Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, at least a portion of the heat required for evaporation of solvent may be provided by heating the spray solution.

The solvent-bearing feed can be spray-dried under a wide variety of conditions and yet still yield solid dispersions with acceptable properties. For example, various types of nozzles can be used to atomize the spray solution, thereby introducing the spray solution into the spray-dry chamber as a collection of small droplets. Essentially any type of nozzle may be used to spray the solution as long as the droplets that are formed are sufficiently small that they dry sufficiently (due to evaporation of solvent) such that they do not stick to or coat the spray-drying chamber wall.

Although the maximum droplet size varies widely as a function of the size, shape and flow pattern within the spray-dryer, generally droplets should be less than about 500 μm in diameter when they exit the nozzle. Examples of types of nozzles that may be used to form the solid dispersions include the two-fluid nozzle, the fountain-type nozzle, the flat fan-type nozzle, the pressure nozzle and the rotary atomizer. In a preferred embodiment, a pressure nozzle is used, as disclosed in detail in U.S. Published Patent Application US 2003-0185893, filed Jan. 24, 2003, the disclosure of which is incorporated herein by reference.

The spray solution can be delivered to the spray nozzle or nozzles at a wide range of temperatures and flow rates. Generally, the spray solution temperature can range anywhere from just above the solvent's freezing point to about 20° C. above its ambient pressure boiling point (by pressurizing the solution) and in some cases even higher. Spray solution flow rates to the spray nozzle can vary over a wide range depending on the type of nozzle, spray-dryer size and spray-dry conditions such as the inlet temperature and flow rate of the drying gas. Generally, the energy for evaporation of solvent from the spray solution in a spray-drying process comes primarily from the drying gas.

The drying gas can, in principle, be essentially any gas, but for safety reasons and to minimize undesirable oxidation of the drug or other materials in the solid dispersion, an inert gas such as nitrogen, nitrogen-enriched air or argon is utilized. The drying gas is typically introduced into the drying chamber at a temperature between about 60° and about 300° C. and preferably between about 80° and about 240° C.

The large surface-to-volume ratio of the droplets and the large driving force for evaporation of solvent leads to rapid solidification times for the droplets. Solidification times should be less than about 20 seconds, preferably less than about 10 seconds, and more preferably less than 1 second. This rapid solidification is often critical to the particles maintaining a uniform, homogeneous dispersion instead of separating into drug-rich and polymer-rich phases. In a preferred embodiment, the height and volume of the spray-dryer are adjusted to provide sufficient time for the droplets to dry prior to impinging on an internal surface of the spray-dryer, as described in detail in U.S. Pat. No. 6,763,607, incorporated herein by reference. As noted above, to obtain large enhancements in concentration and bioavailability it is often necessary to obtain as homogeneous a dispersion as possible.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of drug molecules in the solid dispersion, thereby improving its stability. Generally, the solvent content of the solid dispersion as it leaves the spray-drying chamber should be less than 10 wt % and preferably less than 2 wt %.

Following formation, the solid dispersion can be dried to remove residual solvent using suitable drying processes, such as tray drying, vacuum drying, fluid bed drying, microwave drying, belt drying, rotary drying, and other drying processes known in the art. Preferred secondary drying methods include vacuum drying or tray drying. To minimize chemical degradation during drying, drying may take place under an inert gas such as nitrogen, or may take place under vacuum.

The solid dispersion is usually in the form of small particles. The volumetric mean diameter of the particles may be less than 500 μm, or less than 100 μm in diameter, less than 50 μm in diameter or less than 25 μm in diameter. When the solid dispersion is formed by spray-drying, the resulting dispersion is in the form of such small particles. When the solid dispersion is formed by other methods such by roto-evaporation, precipitation using a non-solvent, spray-coating, melt-congeal, or extrusion processes, the resulting dispersion may be sieved, ground, or otherwise processed to yield a plurality of small particles.

In another embodiment, the solvent is removed by spraying the solvent-bearing feed solution onto seed cores. The seed cores can be made from any suitable material such as starch, microcrystalline cellulose, sugar or wax, by any known method, such as melt- or spray-congealing, extrusion/spheronization, granulation, spray-drying and the like. The feed solution can be sprayed onto such seed cores using coating equipment known in the pharmaceutical arts, such as pan coaters (e.g., Hi-Coater available from Freund Corp. of Tokyo, Japan, Accela-Cota available from Manesty of Liverpool, U.K.), fluidized bed coaters (e.g., Würster coaters or top-sprayers available from Glatt Air Technologies of Ramsey, N.J. and from Niro Pharma Systems of Bubendorf, Switzerland) and rotary granulators (e.g., CF-Granulator, available from Freund Corp). During this process, the seed cores are coated with the feed solution and the solvent is evaporated, resulting in a coating comprising the solid dispersion. Forming the solid dispersion on a seed core has an advantage in that while the dispersion has a low density and thus allows for rapid dissolution when administered to an aqueous use environment, the so-formed particles have an overall density similar to that of the seed core, improving the processing and handling of the composition.

Concentration Enhancement

In a preferred embodiment, the compositions of the present invention are "concentration-enhancing," meaning that a solid dispersion of drug, cationic species, and dispersion polymer improves the concentration of drug in a use environment relative to a control composition consisting essentially of an equivalent amount of drug in the crystalline neutral form. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as Phosphate Buffered Saline (PBS) solution or a Model Fasted Duodenal (MFD) solution. Concentration enhancement may be determined through either in vitro dissolution tests or through in vivo tests. It has been determined that enhanced drug concentration in in vitro dissolution tests in MFD solution or PBS solution is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein there is also present 7.3 mM sodium taurocholic acid and 1.4 mM of 1-palmitoyl-2-oleyl-sn-glycero-3-phosphocholine. In particular, a composition of the present invention may be dissolution-tested by adding it to MFD or PBS solution and agitating to promote dissolution.

In one embodiment, when dosed to an aqueous environment of use, the compositions of the present invention provide a maximum dissolved concentration (MDC) of the drug that is at least 1.25-fold the MDC provided by the control composition, e.g., if the MDC provided by the control composition is 100 μg/mL, then a composition of the present invention provides an MDC of at least 125 μg/mL. It is to be understood that the control composition is free from solubilizers or other components that would materially affect the solubility of the drug, and that the drug is in solid crystalline neutral form in the control composition. Preferably, the inventive compositions provide an MDC of the drug in aqueous solution that is at least 2-fold, and more preferably at least 3-fold. Surprisingly, the inventive compositions may achieve extremely large enhancements in aqueous concentration. In some cases, the MDC of the drug provided by the test composition is at least 5-fold or more the MDC provided by the control.

In another embodiment, the inventive compositions increase the dissolution area under the concentration versus time curve (AUC) of the drug in the environment of use relative to a control composition consisting of an equivalent amount of crystalline neutral form of the drug but with no polymer. More specifically, in the environment of use, the inventive compositions provide an AUC for any 90-minute period of from 0 to 270 minutes following introduction to the use environment that is at least 1.25-fold that of the control composition described above. Preferably, the AUC provided by the composition is at least 2-fold, more preferably at least 3-fold that of the control composition. Some compositions of the present invention may provide an AUC value that is at least 5-fold, and even at least 10-fold or more that of a control composition as described above.

Alternatively, the compositions of the present invention, when dosed orally to a human or other animal, provide an AUC in drug concentration in the blood plasma or serum (or relative bioavailability) that is at least 1.25-fold that observed in comparison to the control composition. Preferably, the blood AUC is at least about 2-fold, more preferably at least about 3-fold, even more preferably at least about 4-fold, still more preferably at least about 6-fold, yet more preferably at least about 10-fold, and most preferably at least about 20-fold that of the control composition. The determination of AUCs is a well-known procedure and is described, for example, in Welling, "Pharmacokinetics Processes and Mathematics," ACS Monograph 185 (1986).

Alternatively, the compositions of the present invention, when dosed orally to a human or other animal, provide a maximum drug concentration in the blood plasma or serum (Cmax) that is at least 1.25-fold that observed in comparison to the control composition. Preferably, the Cmax is at least about 2-fold, more preferably at least about 3-fold, even more preferably at least about 4-fold, still more preferably at least about 6-fold, yet more preferably at least about 10-fold, and most preferably at least about 20-fold that of the control composition. Thus, compositions that meet the in vitro or in vivo performance criteria, or both, are considered to be within the scope of the invention.

Solid Dosage Forms

The compositions may be delivered by a wide variety of routes, including, but not limited to, oral, nasal, rectal, vaginal, subcutaneous, intravenous and pulmonary. Generally, the oral route is preferred.

The compositions may also be used in a wide variety of dosage forms for administration of the drug. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders that are reconstituted by first adding water to one powder to form a solution to which the second powder is combined with agitation to form the suspension.

The compositions of the present invention may also be filled into a suitable capsule, such as a hard gelatin capsule or a soft gelatin capsule, well known in the art (see, for example, *Remington's The Science and Practice of Pharmacy*, 20$^{th}$ Edition, 2000).

Other features and embodiments of the invention will become apparent from the following Examples that are given for illustrating the invention rather than for limiting its intended scope.

EXAMPLES

Drugs Used in Examples

Drug 1 is 6-amino-9-benzyl-8-oxo-8,9-dihydro-7H-purine-2-carboxylic acid cyclopropylmethyl-amide, or pharmaceutically acceptable forms thereof, having the following structure in its neutral form:

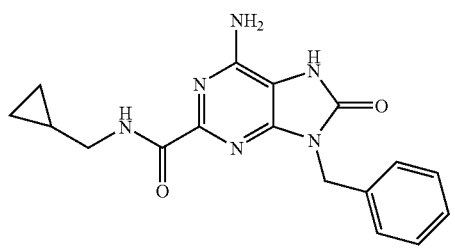 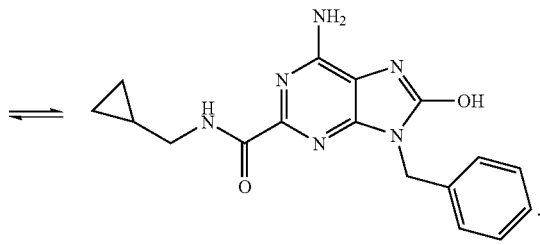

Drug 1 was prepared using the following procedure.

Step 1: Preparation of 9-benzyl-2,6-dichloro-9H-purine

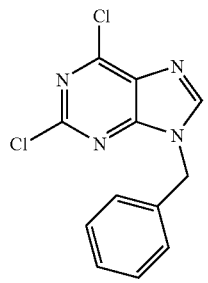 [SMILES: Clc1nc(Cl)c2ncn(Cc3ccccc3)c2n1]

2,6-Dichloro-9H-purine (10.9 g, 60 mmol; purchased from Aldrich Chemical Co.) was dissolved in 200 mL dimethylformamide (DMF) and potassium carbonate (31.9 g, 230 mmol) was added. Benzyl bromide (13.7 mL, 120 mmol) was added in portions and the whole stirred at room temperature under nitrogen for 16 hours. The mixture was filtered through a short plug of Arbocel® and the filtrate was evaporated in vacuo to give a yellow oil of the N7-(more polar) and N9-benzyl (less polar) purines. This oil was purified by silica gel chromatography using 1:2:10 ethylacetate:acetone:hexane as eluent to give the 9-benzyl-2,6-dichloro-9H-purine as a white solid (9.1 g, 57%).

Step 2: Preparation of 9-benzyl-2-chloro-9H-purin-6-ylamine

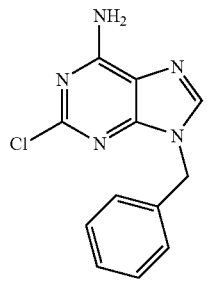 [SMILES: Nc1nc(Cl)nc2c1ncn2Cc1ccccc1]

The product from Step 1 (10 g, 40 mmol) was suspended in ethanol (60 mL) and 70 mL of a concentrated ammonium hydroxide solution (specific gravity of 0.88) was added. The mixture was heated in a steel pressure vessel at 100° C. for 6 h and then allowed to cool to room temperature. The reaction mixture was filtered to provide an off-white solid which was washed with water (15 mL) and ethanol (15 mL) and dried under vacuum to provide the 9-benzyl-2-chloro-9H-purin-6-ylamine as a white solid (8.7 g, 94%).

Step 3: Preparation of 9-benzyl-8-bromo-2-chloro-9H-purin-6-ylamine

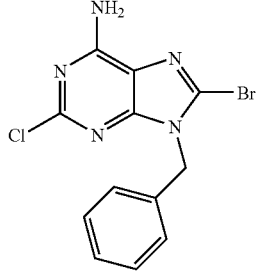 [SMILES: Nc1nc(Cl)nc2c1nc(Br)n2Cc1ccccc1]

The product from Step 2 (3 g, 11.6 mmol) was suspended in acetic acid (50 mL) and sodium acetate (1.4 g, 17.3 mmol) and the mixture cooled in an ice bath while bromine (3.6 mL, 69.3 mmol) was added dropwise. After the addition was complete, the mixture was heated at 70° C. under a nitrogen atmosphere for 5 h and then allowed to cool to room temperature. The mixture was poured onto 50 mL of a 10% aqueous $Na_2S_2O_3$ solution, and the whole reduced in vacuo to approximately 10 mL and then neutralized with 2 N NaOH solution. The organics were extracted with dichloromethane (3×150 mL), washed with water (100 mL) and brine (100 mL) and then dried ($MgSO_4$) and evaporated to a yellow solid. Trituration of the solid with ether and filtration provided an off-white solid of 9-benzyl-8-bromo-2-chloro-9H-purin-6-ylamine (3.3 g, 85%) which was found to be sufficiently pure to be used with no further purification.

Step 4. Preparation of 6-amino-9-benzyl-2-chloro-7,9-dihydro-purin-8-one

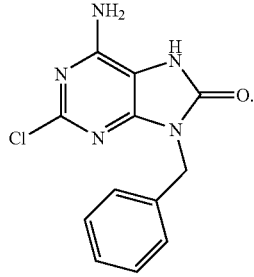 [SMILES: Nc1nc(Cl)nc2c1[nH]c(=O)n2Cc1ccccc1]

The product from Step 3 (2 g, 5.9 mmol) was suspended in 12 N HCl (35 mL) and n-butanol (35 mL) and the mixture heated at 100° C. for 7 h and then allowed to cool to room temperature. The reaction mixture was evaporated to dryness in vacuo, and then partitioned between 2 N NaOH (50 mL) and dichloromethane (50 mL). The organic layer was separated and found to contain some unreacted starting material only and was discarded, while the aqueous layer was neutralized with concentrated HCl and the resulting precipitate collected by filtration and washed with ethyl acetate to give 6-amino-9-benzyl-2-chloro-7,9-dihydro-purin-8-one as an off-white solid (1.5 g, 94%) which was found to be >90% pure and was used with no further purification.

Step 5: Preparation of 6-amino-9-benzyl-8-oxo-8,9-dihydro-7H-purin-2-carboxylic Acid Ethyl Ester

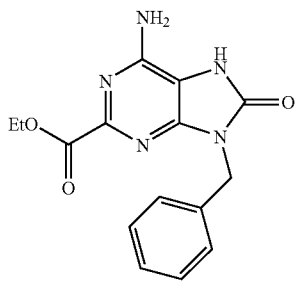 [SMILES: CCOC(=O)c1nc(N)c2[nH]c(=O)n(Cc3ccccc3)c2n1]

The product from Step 4 was suspended in a mixture of ethanol (10 mL) and Na$_2$CO$_3$ in a steel pressure vessel. Pd(diphenylphosphinoferrocenyl)$_2$Cl$_2$ in dichloromethane (30 mg, 0.04 mmol) was added, and the mixture heated at 110° C. under 120 psi (827 kPa) pressure of carbon monoxide for 20 hr. After this time, the mixture was allowed to cool to room temperature and then evaporated under reduced pressure.

The resulting residue was chromatographed on silica gel using 2%, then 5% methanol in dichloromethane as the eluent to give 6-amino-9-benzyl-8-oxo-8,9-dihydro-7H-purin-2-carboxylic acid ethyl ester as an off-white solid (74 mg, 33%).

Step 6: Preparation of Drug 1

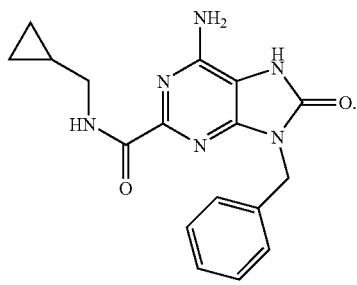 [SMILES: Nc1nc(C(=O)NCC2CC2)nc2c1[nH]c(=O)n2Cc1ccccc1]

The compound of Step 5 (40 mg, 0.13 mmol) was taken up in ethanol (2 mL) and cyclopropylmethylamine (335 µL, 3.8 mmol) in a 5 mL ReactiVial® (Fisher Scientific) and heated at 60° C. for 70 h. A further 335 µL of cyclopropylmethylamine was then added to the vial and heating continued for a further 48 h. The mixture was allowed to cool to room temperature and was then evaporated to dryness under reduced pressure. The resulting residue was slurried with water (2 mL) and then filtered. The white powder collected was found to be >90% pure product and was used with no further purification (32 mg, 74%). An analytically pure sample was obtained by silica gel chromatography using 2%, then 5%, then 10% methanol in dichloromethane as the eluent to provide Drug 1 as a white powder.

The neutral form of Drug 1 has a solubility in a pH 6.5 MFD solution of about 3 µg/mL. Drug 1 has a solubility in acetone of 25 µg/mL, and a solubility in methanol of 59 µg/mL. Drug 1 has an acidic pKa of 7.3, a T$_m$ of >350° C., a T$_g$ estimated to be less than about 140° C., and an estimated T$_m$/T$_g$ ratio of greater than 1.5 (K/K).

Drug 2 is 4-amino-1-benzyl-6-trifluoromethyl-1,3-dihydro-imidazo[4,5-c]pyridine-2-one, or pharmaceutically acceptable forms thereof, having the following structure in its neutral form:

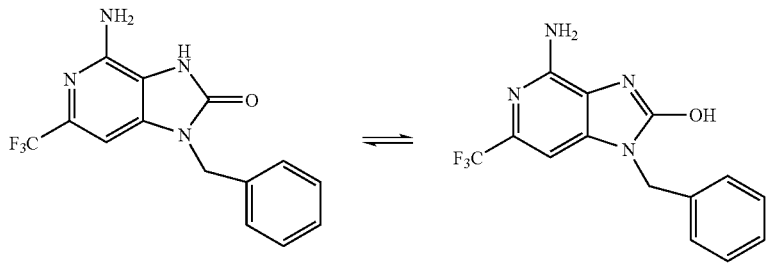 [SMILES: Nc1nc(C(F)(F)F)cc2c1[nH]c(=O)n2Cc1ccccc1 ; Nc1nc(C(F)(F)F)cc2c1nc(O)n2Cc1ccccc1]

Drug 2 was Prepared Using the Following Procedure

Step 1: Preparation of 2,4-Dihydroxy-6-trifluoromethyl-nicotinic Acid Ethyl Ester To dissolve 3-Amino-4,4,4-trifluorocrotonic acid ethyl ester (100 g/546 mmol) in dichloromethane (600 mL) was added pyridine (53 mL/660 mmol). Placed under nitrogen and cooled to 5° C. by suspending in an ice-bath. Ethyl malonyl chloride was added dropwise over approx 1 hr such that temperature did not exceed 20° C. Resulting pale brown solution was stirred at 5° C. for 3 hrs then allowed to warm to room temperature overnight to give a dark green solution. Washed with 1M HCl$_{(aq)}$ (200 mL) then saturated NaHCO$_{3(aq)}$ (250 mL). Aqueous washings sequentially re-extracted with further dichloromethane (2×250 mL). Organics combined, dried over Na$_2$SO$_4$, filtered and concentrated to a dark green oil of crude 3-(2-Ethoxycarbonyl-acetylamino)-4,4,4-trifluoro-but-2-enoic acid ethyl ester (175 g). A portion of the crude (120 g) was dissolved in ethanol (300 mL) and placed under nitrogen. Potassium tert-butoxide (54 g/480 mmol) was added in several portions such that temperature did not exceed 60° C. resulting in a purple solution. Heated at 70° C. for 3 hrs. Added ethanol (100 mL) to reduce viscosity and heated at 80° C. for a further hour. Allowed to cool and concentrated in vacuo to a red solid. Dissolved in water (500 mL) and added citric acid (180 g) causing precipitation. Added ethyl acetate (600 mL). Poured into separating funnel and ran off aqueous. The organic layer containing much undissolved solid was filtered to give the title compound (46.5 g) as a white solid. Concentration of the organic filtrate and trituration with methanol afforded 2,4-dihydroxy-6-trifluoromethyl-nicotinic acid ethyl ester (15.3 g) as a white solid.

Step 2: Preparation of 6-Trifluoromethyl-pyridine-2,4-diol 2,4-Dihydroxy-6-trifluoromethyl-nicotinic acid ethyl ester (62 g/247 mmol) was added in several portions over 30 min to 6M $HCl_{(aq)}$ (620 mL) at reflux. Heated at 100° C. overnight with vigorous stirring to obtain complete solution. Allowed to cool and concentrated in vacuo to a white solid. Slurried in water (250 mL) and adjusted to pH 7 with concentrated ammonia to get heavy white suspension. Collected solid by filtration, rinsing through with fresh water, and dried to provide 6-trifluoromethyl-pyridine-2,4-diol (44.0 g) as a white solid.

Step 3: Preparation of 3-Nitro-6-trifluoromethyl-pyridine-2,4-diol

6-Trifluoromethyl-pyridine-2,4-diol (56 g, 310 mmol) was added in 3-5 gm portions to concentrated sulphuric acid (140 mL) with stirring to give a pale brown solution. The temperature increased to ~50° C. during the addition. Nitric acid (21.1 mL 328 mmol, 70% $HNO_3$ d=1.4 gm/ml) was added drop wise at such a rate as to maintain a reaction temperature of between 45° and 50° C. which took approximately 90 minutes. Once all the nitric acid had been added the reaction was allowed to cool to ambient temperature over 3 hours. Poured into ice/water (~1.3 kg) with stirring, after a few minutes a pale yellow precipitate formed which was filtered off, dissolved in ethyl acetate and dried over sodium sulphate, filtered and evaporated. A second crop of material was obtained by extraction of the aqueous filtrate with ethyl acetate. Combined batches and purified by crystallization from ethyl acetate/n-heptane gave 3-nitro-6-trifluoromethyl-pyridine-2,4-diol as a white 'fluffy' solid (49.5 gm 71% yield).

Step 4: Preparation of 4-Chloro-3-nitro-6-trifluoromethyl-pyridin-2-ol

3-Nitro-6-trifluoromethyl-pyridine-2,4-diol (5.8 gm, 26 mmol) was heated in phenylphosphonic dichloride (30 mL) at 100° C. for 19 hours. Cooled and poured on to ice (60 gm), extracted with ethyl acetate (3×50 mL). The combined organic extracts were washed with aqueous sodium hydrogen carbonate solution (10% w/v) until the washings remained basic (pH ~8). The deep yellow organic layer was then washed with saturated brine, dried over sodium sulphate, filtered and evaporated to give a yellow gum. Trituration of the gum with dichloromethane gave a yellow solid which was filtered off and dried (4.65 gm). The solid was dissolved in water (25 mL) and acidified with 2N hydrochloric acid (7.5 mL) to give a thick white precipitate which was filtered off and washed with water. The precipitate was dissolved in ethyl acetate, dried over sodium sulphate, filtered and evaporated to give 4-chloro-3-nitro-6-trifluoromethyl-pyridin-2-as a white solid (3.75 gm).

Step 5: Preparation of 4-Benzylamino-3-nitro-6-trifluoromethyl-pyridin-2-ol

4-Chloro-3-nitro-6-trifluoromethyl-pyridin-2-ol (65.1 gm 268 mmol) was dissolved in tetrahydrofuran (350 mL) and stirred at room temperature under $N_2$. Benzylamine (86.3 gm 805 mmol) in tetrahydrofuran (50 mL) was added drop wise over 30 minutes to give a bright yellow solution. The reaction was heated in an oil bath at 50° C. for 18 hours, (a solid formed during the reaction). Cooled to ambient temperature, diluted the reaction mixture with diethyl ether (200 mL) and filtered off the solid (benzylamine hydrochloride). The filtrate was evaporated to low bulk under reduced pressure to give a thick yellow slurry. Added diethyl ether (300 mL) and filtered off the yellow solid, dried on the filter pad to give the benzylamine salt (96.5 gm). The desired product was liberated by partition of the solid between aqueous 2N HCl and dichloromethane and crystallization from ethyl acetate/n-pentane gave 4-benzylamino-3-nitro-6-trifluoromethyl-pyridin-2-ol as a pale yellow solid (61.7 gm 73.4% yield).

Step 6: Preparation of Benzyl-(2-chloro-3-nitro-6-trifluoromethyl-pyridin-4-yl)-amine 4-Benzylamino-3-nitro-6-trifluoromethyl-pyridin-2-ol (61.7 gm 197 mmol) was added to phenylphosphonic dichloride (180 mL) and heated to 100° C. in an oil bath, under $N_2$ overnight. The starting material dissolved on heating to give a light yellow solution. Quenched the cooled reaction mixture on to ice water (600 gm of ice+100 mL water) to give a pale yellow solid. Filtered off and washed the solid well with water. The solid was dissolved in ethyl acetate (600 mL) and washed with aqueous sodium hydrogen carbonate solution (10% w/v) until there was no further effervescence and the pH of the aqueous washings were basic. The organic layer was dried over sodium sulphate, filtered and evaporated to give a dirty yellow solid. The solid was dissolved in diethyl ether and to this was added n-hexane until the solution was cloudy, within a few minutes a thick flocculent solid had formed, filtered off, washed with n-hexane and dried to give benzyl-(2-chloro-3-nitro-6-trifluoromethyl-pyridin-4-yl)-amine (60.59 gm 92% yield).

Step 7: Preparation of Ethyl-[2-chloro-3-nitro-6-(trifluoromethyl)-pyridin-4-yl]-benzylcarbamate Benzyl-(2-chloro-3-nitro-6-trifluoromethyl-pyridin-4-yl)-amine (57 gm 170 mmol) was dissolved in tetrahydrofuran (750 mL) and stirred under $N_2$. Cooled in an ice/salt bath to −5° C. To this solution was added drop wise over a period of ~30 minutes, a solution of potassium t-butoxide (21.2 gm, 189 mmol) in tetrahydrofuran (200 mL), maintaining the temperature between −5° and 0° C. to give a deep red reaction mixture. Stirred at this temperature for 15 minutes before the drop wise addition of a solution of ethyl chloroformate (21.4 gm, 198 mmol) in tetrahydrofuran (100 mL), keeping the temperature below 5° C. The cooling bath was removed and the reaction mixture was allowed to reach ambient temperature over 1 hour to give a light brown hazy solution. Evaporation of the solvent was followed by partition of the residue between saturated brine (50 mL) and t-butyl methyl ether (300 mL). The organic phase was washed with water (50 mL) followed by saturated brine (50 mL), dried over sodium sulphate, filtered and evaporated to give a brown oil. The oil was dissolved in n-pentane (250 mL) and stored at ambient temperature overnight. The n-pentane solution was decanted from a dark brown tar which had precipitated out. Evaporation of the solvent gave ethyl-[2-chloro-3-nitro-6-(trifluoromethyl)-pyridin-4-yl]-benzylcarbamate as a pale brown viscous oil (63 gm, 91% yield).

Step 8: Preparation of Ethyl-[2-amino-3-nitro-6-(trifluoromethyl)-pyridin-4-yl]-benzylcarbamate Ethyl-[2-chloro-3-nitro-6-(trifluoromethyl)-pyridin-4-yl]-benzylcarbamate (63 gm 160 mmol) was dissolved in tetrahydrofuran (300 mL) and to this was added concentrated ammonia hydroxide solution (0.88 specific gravity, 100 mL) to give two phases. This was transferred to a pressure vessel, sealed and heated to 80° C. with stirring for 2 hours. The tetrahydrofuran was evaporated and the residue was partitioned between saturated brine and diethyl ether. The organic extracts were dried over sodium sulphate, filtered and evaporated to give a thick yellow slurry (65 gm) of ethyl-[2-amino-3-nitro-6-(trifluoromethyl)-pyridin-4-yl]-benzylcarbamate.

Step 9: Preparation of Ethyl-[2,3-diamino-6-(trifluoromethyl)-pyridin-4-yl]-benzylcarbamate Crude ethyl-[2-amino-3-nitro-6-(trifluoromethyl)-pyridin-4-yl]-benzylcarbamate (65 gm, 170 mmol) was dissolved in ethanol (1000 mL) and 10% Pd—C (6 g m) was added. Hydrogenation at 40° C. and 40 psi for 1 hour gave complete reduction of the nitro group. The catalyst was removed by filtration and the filtrate evaporated to dryness under reduced pressure to give a light brown semi-solid. Trituration with t-butyl methyl ether (150 mL) followed by filtration and washing with the same solvent (30 mL) gave ethyl-[2,3-diamino-6-(trifluoromethyl)-pyridin-4-yl]-benzylcarbamate (36 gm, 60% yield) as a white solid.

Step 10: Preparation of Drug 2

Ethyl-[2,3-diamino-6-(trifluoromethyl)-pyridin-4-yl]-benzylcarbamate (35 gm 99 mmol) was dissolved in glacial acetic acid (300 mL) at room temperature. Filtered to remove any insoluble material and then the clear yellow filtrate was heated with stirring to 80° C. Within 10 minutes a white precipitate began to form. Heating was continued for a total of 40 minutes. The reaction mixture was allowed to cool to ambient temperature and the precipitate was collected by filtration, washed with acetic acid and dried in vacuo at 50° C. for 3 hours to give Drug 2 (26.4 gm, 86% yield) as a white solid.

The neutral form of Drug 2 has a solubility in a pH 6.5 MFD solution of about 1 μg/mL. Drug 2 has a solubility in acetone of <1 mg/mL, and a solubility in methanol of <1 mg/mL. Drug 2 has an acidic pKa of 11.3, a $T_m$ of >350° C., a $T_g$ estimated to be less than about 140° C., and an estimated $T_m/T_g$ ratio of greater than 1.5 (K/K).

Drug 3 is 6-(5-chloro-3-methyl-benzofuran-2-sulfonyl)-2H-pyridazin-3-one, or pharmaceutically acceptable forms thereof, having the following structure in its neutral form:

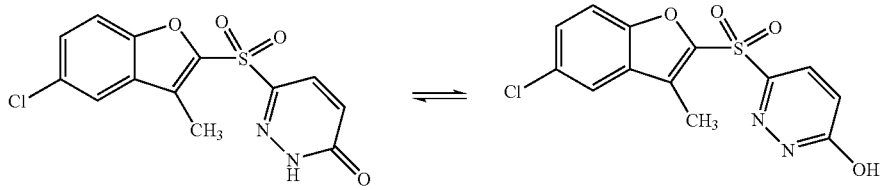 [SMILES: Cc1c(S(=O)(=O)c2ccc(=O)[nH]n2)oc2ccc(Cl)cc12 ; Cc1c(S(=O)(=O)c2ccc(O)nn2)oc2ccc(Cl)cc12]

Drug 3 may be synthesized by standard organic synthesis techniques using the procedures described in U.S. Pat. No. 6,579,879, the disclosure of which is herein incorporated by reference.

The neutral form of Drug 3 has a solubility in phosphate buffered saline solution at pH of 6.5 of less than 1 μg/mL, a solubility in methanol at 25° C. of about 1.5 mg/mL, a solubility in acetone at 25° C. of about 4.7 mg/mL, and a solubility in THF at 25° C. of about 12 mg/mL. Drug 3 has an acidic pKa of 6.9, a $T_m$ of 258° C., a $T_g$ of 74° C., and a $T_m/T_g$ ratio of 1.53 (K/K).

Examples 1 and 2

Solid spray-dried dispersions of Drug 1 and HPMC (E3 Prem LV, Methocel®, available from Dow Chemical Company, Midland, Mich.) were prepared as follows. For the solid dispersion of Example 1, a spray solution was formed containing 1.98 g water, 7.92 g methanol, and 140 μL 1 M KOH (containing 5.5 mg potassium cations), to which was added 25 mg of the crystalline neutral form of Drug 1. Next, 75 mg HPMC was added to the solution and the solution was stirred for 5 minutes and sonicated for 2 minutes, effectively dissolving all of the solid material into the solvent. For the solid dispersion of Example 2, a spray solution was formed containing 4.95 g water, 19.8 g methanol, and 110 μL 1 M KOH (containing 4.3 mg potassium cations), to which was added 25 mg of the crystalline neutral form of Drug 1. Next, 225 mg HPMC was added to the solution and the solution was stirred for 5 minutes and sonicated for 2 minutes.

In separate experiments, each solution was pumped via a Cole Parmer 74900 series rate-controlling syringe pump at a rate of 0.65 ml/min into a small-scale spray-drying apparatus consisting of an 11-cm diameter stainless steel chamber. The drug/polymer solution was atomized through a two-fluid nozzle (Spraying Systems Co., Wheaton, Ill., Model No. SU1A) using a heated stream of nitrogen at a flow rate of 0.55 standard ft³/min. The heated gas entered the chamber at an inlet temperature of 85° C. and exited at an outlet temperature of 22° C. The resulting solid dispersion was collected on filter paper, dried under vacuum, and stored in a desiccator. The dispersion of Example 1 contained 23.7 wt % Drug 1, 5.2 wt % potassium cations, and 71.1 wt % HPMC, while the dispersion of Example 2 contained 9.8 wt % Drug 1, 1.7 wt % potassium cations, and 88.5 wt % HPMC.

In Vitro Dissolution Tests

These tests demonstrate that the solid dispersion of the invention increases the concentration of dissolved Drug 1 in vitro. For these tests, suspensions were formed by adding a sufficient quantity of the dispersions of Example 1 or Example 2 to water containing 0.5 wt % Methocel Type A such that each suspension contained 7.2 mgA/mL Drug 1. Next, a 50 μL sample of each suspension was added to microcentrifuge tubes in duplicate. The tubes were placed in a 37° C. temperature-controlled chamber, and 1.75 mL MFD solution was added to each respective tube. The concentration of dissolved Drug 1 in each tube would have been 200 μgA/mL, if all of Drug 1 had dissolved. The samples were quickly mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high-performance liquid chromatography (HPLC). HPLC analysis was performed using an Zorbax RX-$C_{18}$ 4.6×75 mm 3.5 μM column, with a mobile phase of 63/37 v/v aqueous 0.1 wt % trifluoroacetic acid/acetonitrile, and UV absorbance measured at 220 nm. The contents of each respective tube were mixed on the vortex mixer and allowed to stand undisturbed at 37° C. until the next sample was taken. Samples were collected at 4, 10, 20, 40, 90, and 1200 minutes.

Control 1

Control 1 consisted of the crystalline neutral form of Drug 1 in a 7.2 mgA/mL suspension in 0.5 wt % Methocel A, and a sufficient amount of material was added so that the concentration of dissolved Drug 1 would have been 200 μgA/mL, if all of Drug 1 had dissolved.

The concentrations of dissolved Drug 1 obtained in these samples were used to determine the maximum dissolved concentration of Drug 1 in solution during the first ninety minutes of the test ($MDC_{90}$), the area under the concentration-versus-time curve during the initial ninety minutes ("$AUC_{90}$"), and the concentration of Drug 1 at 1200 minutes ("$C_{1200}$"). The results are shown in Table 1.

TABLE 1

| Sample | $MDC_{90}$ (μg/mL) | $AUC_{90}$ (min*μg/mL) | $C_{1200}$ (μg/mL) |
|---|---|---|---|
| Example 1 | 23 | 1,800 | 17 |
| Example 2 | 24 | 1,700 | 9 |
| Control 1 Crystalline neutral form of Drug 1 | 1 | <88 | <0.1 |

As can be seen from the data, the solid dispersions of the invention increased the concentration of dissolved Drug 1 over that provided by crystalline Drug 1 alone. The solid dispersion of Example 1 provided an $MDC_{90}$ value that was 23-fold that provided by the crystalline control, and an $AUC_{90}$ value that was more than 20-fold that provided by the crystalline control. The solid dispersion of Example 2 provided an $MDC_{90}$ value that was 24-fold that provided by the crystalline control, and an $AUC_{90}$ value that was more than 19-fold that provided by the crystalline control.

Example 3

A solid dispersion containing Drug 1 and HPMC was prepared as follows. First, 6765 g methanol, 1197 g water, 41 mL 5 M potassium hydroxide (containing 8 g potassium cations), and 40 g crystalline neutral form of Drug 1 were weighed into a stainless steel tank equipped with an overhead agitator. The solution was stirred overnight, completely dissolving the drug. Next, 111.98 g HPMC (E3 Prem) was added directly to this mixture, and the mixture stirred to dissolve the HPMC, forming the spray solution.

The spray solution was pumped using a high-pressure pump to a spray drier (a Niro type XP Portable Spray-Drier with a Liquid-Feed Process Vessel ("PSD-1")), equipped with a pressure-swirl atomizer (Schlick #1.5 pressure nozzle from Dusen Schlick GmbH of Untersiemau, Germany). The PSD-1 was equipped with both 9-inch and 4-inch chamber extensions. The chamber extensions were added to the spray drier to increase the vertical length of the drier. The added length increased the residence time within the drier, which allowed the product to dry before reaching the angled section of the spray drier. A Bran+Lubbe high-pressure pump was used to deliver liquid to the nozzle. The spray solution was pumped to the spray drier at about 40 g/min at a pressure of 485 psig (34 atm). Drying gas (nitrogen) was delivered to the drying chamber at an inlet temperature of 117° C. at an average flow rate of about 1775 g/min. The evaporated solvent and drying gas exited the spray drier at a temperature of about 60° C. The resulting solid dispersion was collected in a cyclone. The dispersion contained 25 wt % A Drug 1, 5 wt % potassium cations, and 70 wt % HPMC.

The solid dispersion formed using the above procedure was dried in a vacuum desiccator before further use.

PXRD Analysis

A sample of the solid dispersion of Example 3 was analyzed using powder x-ray diffraction (PXRD) with a Bruker AXS (Madison, Wis.) D8 Advance diffractometer. A sample (approximately 100 mg) was packed in Lucite sample cups fitted with Si(511) plates as the bottom of the cup to give no background signal. The sample was spun in the φ plane at a rate of 30 rpm to minimize crystal orientation effects. The x-ray source ($KCu_\alpha$, $\lambda=1.54$ Å) was operated at a voltage of 45 kV and a current of 40 mA. Data the sample was collected over a period of 27 minutes in continuous detector scan mode at a scan speed of 1.8 seconds/step and a step size of 0.04°/step. The diffractogram was collected over the 2θ range of 4° to 40°. The results of this analysis, shown in FIG. 1, showed only an amorphous halo, indicating that Drug 1 in the dispersion was almost completely non-crystalline.

Example 4

A solid dispersion of Drug 2 and hydroxypropyl methyl cellulose (HPMC E3 Prem LV, Methocel®, available from Dow Chemical Company, Midland, Mich.) was prepared as follows. First, a spray solution was formed containing 2.97 g water, 16.83 g methanol, and 250 µL 1M KOH (containing 9.8 mg potassium cations), to which was added 51.27 mg of the crystalline neutral form of Drug 2. Next, 140.4 mg HPMC was added to the solution and the solution was stirred for 5 minutes and sonicated for 2 minutes. The solution was pumped via a Cole Parmer 74900 series rate-controlling syringe pump at a rate of 1.1 mL/min into a small-scale spray-drying apparatus described in Example 1. The solution was atomized through a two-fluid nozzle (Spraying Systems Co., Wheaton, Ill., Model No. SU1A) using a heated stream of nitrogen at a flow rate of 1 standard ft$^3$/min. The heated gas entered the chamber at an inlet temperature of 85° C. and exited at an outlet temperature of 22° C. The resulting solid dispersion was collected on filter paper, dried under vacuum, and stored in a desiccator. The solid dispersion contained 25.4 wt % Drug 2, 4.9 wt % potassium cations, and 69.7 wt % HPMC. The yield was about 60%.

PXRD Analysis

Figure 2:
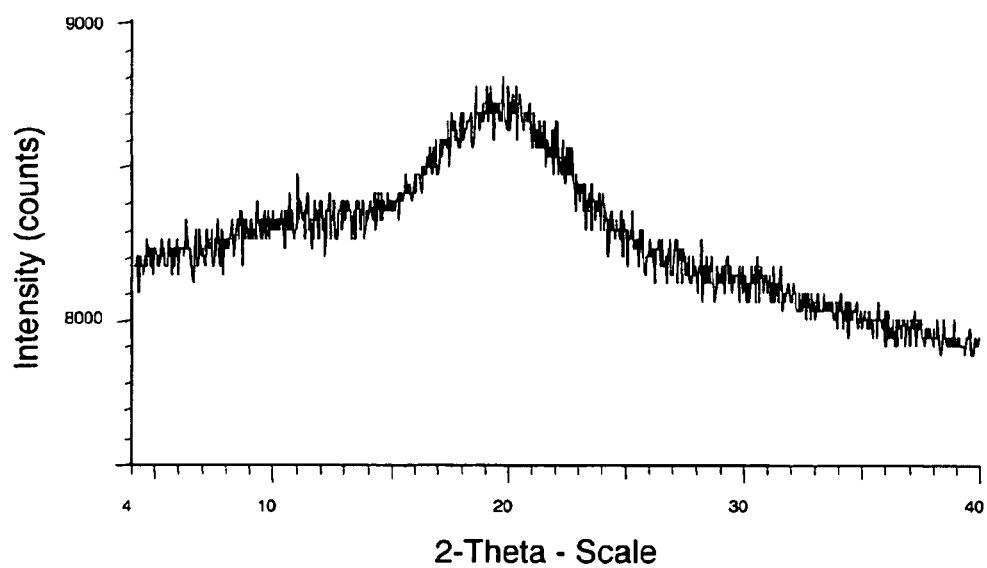
FIG. 2 shows a PXRD diffractogram of the solid dispersion of Example 4.

Samples of the solid dispersion of Example 4 were examined using powder x-ray diffraction (PXRD) with a Bruker AXS (Madison, Wis.) D8 Advance diffractometer, as described in Example 1. The results of this analysis, shown in FIG. 2, showed only an amorphous halo, indicating that Drug 2 in the solid dispersion was almost completely non-crystalline.

In Vitro Dissolution Tests

These tests demonstrate that the solid dispersion of the invention increases the concentration of dissolved Drug 2 in vitro. For this test, a suspension was formed by adding a sufficient quantity of the dispersion of Example 4 to water containing 0.5 wt % Methocel Type A such that the suspension contained 7.2 mgA/mL Drug 2. Next, a 50 µL sample of this suspension was added to microcentrifuge tubes in duplicate. The tubes were placed in a 37° C. temperature-controlled chamber, and 1.75 mL MFD solution was added to each respective tube. The concentration of dissolved Drug 2 in each tube would have been 200 µgA/mL, if all of Drug 2 had dissolved. The samples were quickly mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high-performance liquid chromatography (HPLC). HPLC analysis was performed using an Agilent RX-C$_{18}$ 4.6×75 mm 3.5 µM column, with a mobile phase of 65/35 v/v 0.1 wt % trifluoroacetic acid/acetonitrile, and UV absorbance measured at 220 nm. The contents of each respective tube were mixed on the vortex mixer and allowed to stand undisturbed at 37° C. until the next sample was taken. Samples were collected at 4, 10, 20, 40, 90, and 1200 minutes.

Control 2

Control 2 consisted of the crystalline neutral form of Drug 2 in a 7.2 mgA/mL suspension in 0.5 wt % Methocel A, and a sufficient amount of material was added so that the concentration of dissolved Drug 2 would have been 200 µgA/mL, if all of Drug 2 had dissolved.

The concentrations of dissolved Drug 2 obtained in these samples were used to determine the maximum dissolved concentration of Drug 2 in solution during the first ninety minutes of the test (MDC$_{90}$), the area under the concentration-versus-time curve during the initial ninety minutes ("AUC$_{90}$"), and the concentration of Drug 2 at 1200 minutes ("C$_{1200}$"). The results are shown in Table 2.

TABLE 2

| Sample | MDC$_{90}$ (µg/mL) | AUC$_{90}$ (min*µg/mL) | C$_{1200}$ (µg/mL) |
|---|---|---|---|
| Example 4 | 19 | 1500 | 14 |
| Control 2 Crystalline neutral form of Drug 2 | 0.6 | 44 | 1.0 |

As can be seen from the data, the solid dispersion of the invention increased the concentration of dissolved Drug 2 over that provided by crystalline Drug 2 alone, with the MDC$_{90}$ 31.7-fold that of the control, and the AUC$_{90}$ 34.1-fold that of the control.

Chemical Stability

These tests demonstrate the chemical stability of Drug 2 in a solid dispersion with storage under controlled temperature and humidity conditions to accelerate aging of the dispersion. The potency of Drug 2 in the solid dispersion of Example 4 was measured before and after storage for 1 day at 50° C./75% relative humidity (RH).

To measure potency, approximately 0.6 mg of the solid dispersion was accurately weighed into a volumetric flask, and 10 mL methanol was added. The flask was sonicated to dissolve Drug 2, and analyzed using HPLC. The results are shown in Table 3.

TABLE 3

| Sample | Initial Potency (mgA/g) | Potency following storage at 50° C./75% RH (mgA/g) |
|---|---|---|
| Example 4 Solid Dispersion | 238 ± 1 | 235 ± 4 |

The results above indicate that Drug 2 in the dispersion of Example 4 is stable under these accelerated storage conditions.

Example 5

A solid dispersion containing Drug 3 and HPMC (E3 Prem, available from Dow Chemical Company, Midland, Mich.) was prepared as follows. First, 3306 g methanol, 555.7 g water, 280.9 g 1 M potassium hydroxide, and 87.0 g crystalline neutral form of Drug 3 were weighed into a flask. The solution was stirred about 45 minutes to completely dissolve Drug 3. Next, 120.0 g HPMC was added directly to this mixture, and the mixture stirred for an additional hour to dissolve the HPMC, forming the spray solution.

The spray solution was spray dried using the procedures outlined in Example 3 with the following exceptions. The atomizer was a Schlick #2.5 pressure nozzle and the spray solution was pumped to the spray drier at about 55 g/min at a pressure of 126 psig (9.6 atm). Drying gas (nitrogen) was delivered through the diffuser plate at an inlet temperature of 115° C. The evaporated solvent and drying gas exited the spray drier at a temperature of 55° C. The resulting solid dispersion was collected in a cyclone. The dispersion contained 39.9 wt % A Drug 3 ("wt % A" means the weight percent of the dispersion that is the active, neutral form of Drug 3, having a molecular weight of 324.7 gm/mol), 5 wt % potassium cations, and 55.1 wt % HPMC.

The solid dispersion formed using the above procedure was post-dried using a Gruenberg single-pass convection tray dryer operating at 30° C./15% relative humidity (RH) for a minimum of 5 hours. Following drying, the dispersion was then equilibrated at 21° C. (ambient)/40% RH prior to storage.

PXRD Analysis

Figure 3:
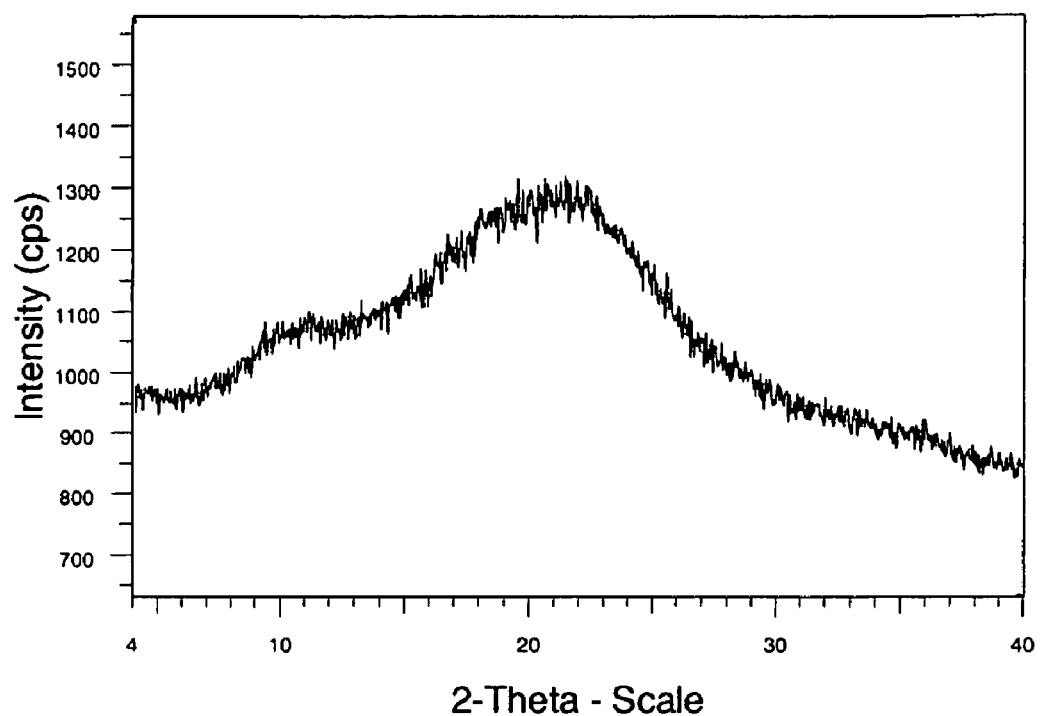
FIG. 3 shows a PXRD diffractogram of the solid dispersion of Example 5.

The solid dispersion of Example 5 was analyzed by PXRD using the procedure outlined in Example 3. The results of this analysis, shown in FIG. 3, showed only an amorphous halo, indicating that Drug 3 in the dispersion was almost completely non-crystalline.

In Vitro Dissolution Test

An in vitro dissolution test was performed to determine the dissolution performance of the solid dispersion of Example 5 relative to the crystalline neutral form of Drug 3 (Control 3). For this test, a sufficient amount of material was added to a microcentrifuge test tube so that the concentration of Drug 3 would have been 200 µgA/mL, if all of the compound had dissolved. The test was run in duplicate. The tubes were placed in a 37° C. temperature-controlled chamber, and 1.8 mL MFD solution at pH 6.5 and 290 mOsm/kg, was added to each respective tube. The samples were quickly mixed using a vortex mixer for about 60 seconds. The samples were centrifuged at 13,000 G at 37° C. for 1 minute. The resulting supernatant solution was then sampled and diluted 1:6 (by volume) with methanol and analyzed by high-performance liquid chromatography (HPLC). HPLC analysis was performed using a Waters Symmetry $C_8$ column. The mobile phase consisted of 45% 20 mM $KH_2PO_4$, adjusted to pH 3, 30% acetonitrile, and 25% methanol. UV absorbance was measured at 270 nm. The contents of each tube were mixed on the vortex mixer and allowed to stand undisturbed at 37° C. until the next sample was taken. Samples were collected at 4, 10, 20, 40, 90, and 1200 minutes.

A similar test was performed with Control 3, and a sufficient amount of material was added so that the concentration of Drug 3 would have been 200 µgA/mL, if all of the compound had dissolved.

The concentrations of Drug 3 obtained in these samples were used to determine the maximum dissolved concentration of Drug 3 ("$MDC_{90}$") and the area under the concentration-versus-time curve ("$AUC_{90}$") during the initial ninety minutes. The results are shown in Table 4.

TABLE 4

| Sample | $MDC_{90}$ (µgA/mL) | $AUC_{90}$ (min*µgA/mL) |
|---|---|---|
| Example 5 | 37 | 2,800 |
| Control 3 (Crystalline neutral form of Drug 3) | 8 | 540 |

The results show that the solid dispersion of Drug 3 provides concentration-enhancement relative to the crystalline neutral form of Drug 3 alone. The dispersion provided an $MDC_{90}$ that was 4.6-fold that provided by Control 3, and an $AUC_{90}$ that was 5.2-fold that provided by Control 3.

Examples 6 and 7

Solid dispersions of Drug 3 and HPMC were prepared as follows. For Example 6, a spray solution was formed by dissolving crystalline neutral form of Drug 3, HPMC, and n-methylglucamine (40/36/24 w/w/w) in methanol. For Example 7, a spray solution was formed by dissolving crystalline neutral form of Drug 3, HPMC, and sodium hydroxide (39/56/5 w/w/w) in methanol. The solutions were pumped into a small-scale spray-drying apparatus via a Cole Parmer 74900 series rate-controlling syringe pump at a rate of 1.3 ml/min. The Drug 3/polymer solution was atomized through a Spraying Systems Co. two-fluid nozzle, Model No. SU1A using a heated stream of nitrogen at a flow rate of 1 standard cubic feet per minute (28 standard L/min). The spray solution was sprayed into an 11-cm diameter stainless steel chamber. Heated nitrogen entered the chamber at an inlet temperature of 70° C. and exited at an ambient outlet temperature. The resulting solid dispersions were collected on filter paper, dried under vacuum, and stored in a desiccator.

Example 8

A solid dispersion of Drug 3 and HPMC was prepared as follows. A spray solution was formed by first adding 0.616 mL of 1 N KOH to 12 gm of a 5/1 (w/w) methanol/water solvent. To this solution was then added 200 mg of the crystalline neutral form of Drug 3 and 800 mg of HPMC, forming the spray solution. The solid dispersion was then formed by spray drying this solution in a small-scale spray-drying apparatus using the procedures outlined for Examples 6-7. The resulting solid dispersion contained about 19.3 wt % A Drug 3.

The dissolution performance of the solid dispersion of Example 8 was evaluated using the procedures outlined in Example 5 with the following exceptions. A 25-mg sample of the dispersion of Example 8 was suspended in 0.5 mL of a suspension media containing 0.5 wt % Methocel Type A and 15 mg/mL HPMCAS-HF dissolved in PBS at pH 6.5. A sufficient quantity of this suspension was then administered to 1.8 mL of MFD solution so that the concentration of Drug 3 would have been 200 µgA/mL, if all of the compound had dissolved. The solution was then analyzed for dissolved Drug 3 concentration versus time, as previously described. The results of this test are summarized in Table 5. Also included in this table are the results for the crystalline neutral form of Drug 3 (Control 3). These data show that the solid dispersion of Example 8 provided an $MDC_{90}$ that was 5.3-fold that provided by Control 3, and an $AUC_{90}$ that was 6.7-fold that provided by Control 3.

TABLE 5

| Sample | $MDC_{90}$ (μgA/mL) | $AUC_{90}$ (min*μgA/mL) |
|---|---|---|
| Example 8 | 42 | 3,600 |
| Control 3 (Crystalline neutral form of Drug 3) | 8 | 540 |

Example 9

The potassium salt form of Drug 3 was prepared as follows. A 414-mg sample of the crystalline neutral form of Drug 3 was added to a 125-mL flask, to which was added 40 mL of acetone. The solution was heated to 60° C. in a hot water bath with stirring to dissolve Drug 3. Once dissolved, 700 μL of 2N KOH was added to the solution, resulting in the immediate formation of a crystalline precipitate of the potassium salt form of Drug 3. The solution was allowed to cool to room temperature. The precipitate was collected by filtration, rinsing the precipitate with several volumes of acetone. The precipitate was then placed in a vacuum desiccator overnight to remove residual acetone.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A solid dispersion, comprising:
   (a) a poorly water soluble ionizable drug, the neutral form of said drug having
      (i) a solubility of less than 1 mg/mL in aqueous solution at a pH between 6 and 7,
      (ii) a solubility of less than 20 mg/mL in a volatile organic solvent, and
      (iii) an acidic pKa value of greater than 5;
   (b) a cationic species; and
   (c) a dispersion polymer wherein said drug is not 6-amino-9-benzyl-8-oxo-8,9-dihydro-7H-purine-2-carboxylic acid cyclopropylmethylamide, at least 90 wt % of said drug in said solid dispersion is in a non-crystalline form and said drug, said cationic species, and said dispersion polymer constitute at least 80 wt % of said solid dispersion, wherein said dispersion polymer is selected from the group consisting of hydroxypropyl methylcellulose, hydroxypropyl methylcellulose acetate, hydroxypropyl cellulose, poloxamers, neutralized forms of hydroxypropyl methylcellulose acetate succinate, neutralized forms of hydroxypropyl methylcellulose phthalate, neutralized forms of cellulose acetate phthalate, neutralized forms of cellulose acetate trimellitate, neutralized forms of carboxymethyl ethyl cellulose, and mixtures thereof.

2. The solid dispersion of claim 1 wherein said drug in its neutral form exists in a keto/enol form.

3. The solid dispersion of claim 1 wherein said drug has an acidic pKa value of greater than 6.

4. The solid dispersion of claim 1 wherein said drug has a ratio of melting point to glass-transition temperature in degrees Kelvin of greater than 1.4.

5. The solid dispersion of claim 1 wherein said dispersion polymer is hydroxypropyl methylcellulose.

6. The solid dispersion of claim 1 wherein said cationic species is selected from the group consisting of cations of potassium, sodium, calcium, magnesium, aluminum, ammonium, and mixtures thereof.

7. The solid dispersion of claim 1 wherein said dispersion has a glass transition temperature that is different than the glass transition temperature of either said drug alone or said polymer alone.

* * * * *